(12) United States Patent
Zhu et al.

(10) Patent No.: US 11,864,772 B2
(45) Date of Patent: Jan. 9, 2024

(54) TOURNIQUET

(71) Applicant: ENODAR MEDICAL (SHANGHAI) CO., LTD., Shanghai (CN)

(72) Inventors: Dawei Zhu, Shanghai (CN); Bifeng Shen, Shanghai (CN); Lianghui Fu, Shanghai (CN); Xinyu Shen, Shanghai (CN); Minjie He, Shanghai (CN)

(73) Assignee: ENODAR MEDICAL (SHANGHAI) CO., LTD., Shanghai (CN)

( * ) Notice: Subject to any disclaimer, the term of this patent is extended or adjusted under 35 U.S.C. 154(b) by 411 days.

(21) Appl. No.: 17/160,101

(22) Filed: Jan. 27, 2021

(65) Prior Publication Data

US 2021/0145454 A1    May 20, 2021

Related U.S. Application Data

(63) Continuation-in-part of application No. PCT/CN2019/097359, filed on Jul. 23, 2019.

(30) Foreign Application Priority Data

Apr. 16, 2019  (CN) .......................... 201910305763.X

(51) Int. Cl.
*A61B 17/132*       (2006.01)
*G04F 10/00*        (2006.01)
(Continued)

(52) U.S. Cl.
CPC .......... *A61B 17/1325* (2013.01); *G04F 10/00* (2013.01); *A61B 2017/00128* (2013.01);
(Continued)

(58) Field of Classification Search
CPC .............. A61B 17/132; A61B 17/1322; A61B 17/1325; A61B 2017/12004;
(Continued)

(56) References Cited

U.S. PATENT DOCUMENTS

2012/0191127 A1* 7/2012 Guillot ............... A61B 17/1325
606/203

FOREIGN PATENT DOCUMENTS

CN        200977177 Y       11/2007
CN        102379733 A   *    3/2012
(Continued)

*Primary Examiner* — Wade Miles
*Assistant Examiner* — Bridget E. Rabaglia
(74) *Attorney, Agent, or Firm* — NKL Law; Allen Xue

(57) ABSTRACT

Disclosed is a tourniquet, comprising a fixing module, a hemostasis module, and an indication module. A floating nut is arranged around a pressure stud, with the upper end of the floating nut being fixedly connected to a rotary knob, and the lower end of the floating nut being provided with a support part; the spinning press block is arranged around the floating nut, with an inner side of the spinning press block abutting against the floating nut, an outer side of the spinning press block being in thread-fit connection with an inner side of a protrusion, and the lower end of the spinning press block being supported by the support part; the spinning press block is provided with a holding hole penetrating through from top to bottom; the spring is sheathed outside the floating nut, with the upper end of the spring abutting against the top face of the protrusion, and the lower end thereof abutting against the upper end of the spinning press block; the connecting piece is disposed in the holding hole; the connecting piece does not rise along with the spinning press block, but rotates along with the spinning press block, and the lower end of the connecting piece is fixedly connected to the pointer; and the pointer rotates along with the connecting piece to point to different pressure values on the dial plate; a time device can also be provided to measure the hemostasis time; the tourniquet can be locked. The present invention is simple in terms of structure and easy to process, easier to observation of the value of applied pressure, highly precise, convenient timekeeping, and safer.

19 Claims, 23 Drawing Sheets

(51) Int. Cl.
*A61B 17/00* (2006.01)
*A61B 17/12* (2006.01)

(52) U.S. Cl.
CPC ............... *A61B 2017/00367* (2013.01); *A61B 2017/00477* (2013.01); *A61B 2017/12004* (2013.01)

(58) Field of Classification Search
CPC ........ A61B 2017/00477; A61B 17/135; A61B 5/022; A61B 2017/00128; G04F 10/00
USPC .................................. 606/201, 202, 203, 204
See application file for complete search history.

(56) References Cited

FOREIGN PATENT DOCUMENTS

| | | |
|---|---|---|
| CN | 102379733 A | 3/2012 |
| CN | 102548490 A | 7/2012 |
| CN | 206026383 U | 3/2017 |
| CN | 109846525 A | 6/2019 |

\* cited by examiner

TOURNIQUET

TECHNICAL FIELD

The present invention relates to the field of medical equipment, and more specifically to a tourniquet.

BACKGROUND ART

At present, after the puncture needle or indwelling needle is removed in a puncture operation (such as transradial artery or femoral artery intervention), the bleeding is usually stopped by finger compression. However, due to manual pressure to stop bleeding, it is difficult to maintain a stable implementation force, which often results in failure of hemostasis, requiring re-pressing to stop bleeding. On the one hand, it increases the labor intensity of medical staff and on the other hand causes pain to patients. In the prior art, hemostasis is also performed by a tourniquet. However, the tourniquet in the prior art has the problem that the pressure adjustment is not easy to control. Some tourniquets have no pressure display. Certain tourniquets have a pressure display, however such pressure display is difficult to observe and has a poor indicative effect, so that it is inconvenient for a doctor to adjust. In addition, since the existing tourniquet has no safety design, the patient can adjust the pressure privately, leading to the risk of bleeding.

Therefore, the art still lacks a safer tourniquet that can accurately display the pressure value, facilitate observation when pressure is applied, and is easy to adjust.

SUMMARY OF THE INVENTION

The purpose of the present invention is to provide a tourniquet. The tourniquet of the present invention is simpler in structure, and easier to process. The applied pressure value is more convenient to observe, with higher accuracy. It is easier to adjust the applied pressure, and convenient for timing, especially preventing non-medical personnel regulate the pressure privately.

In the first aspect of the present invention, a tourniquet is provided. The tourniquet comprises a fixing module, which includes a belt plate and a connecting belt; wherein the belt plate comprises a through hole and a protrusion formed by extending upward from circumference side of the through hole and retracting inwardly at a top end to form an annular opening, and the both ends of the belt plate are respectively connected to the both ends of the connecting belt which has an adjustable length; a hemostatic module, which includes a knob, a pressure stud, and a hemostatic pad; wherein the knob is wrapped around the protrusion and rotatable relative to the protrusion; the pressure stud penetrates the knob and the protrusion, and the upper part of the pressure stud is threadedly connected with the knob, and the lower end of the pressure stud is fixedly connected with the hemostatic pad, and the pressure stud threadedly matched with the knob moves downward by rotating the knob to drive the hemostatic pad to press down; and an indication module, which includes a floating nut, a spinning press block, a spring, a connecting piece, a pointer and a dial; wherein the floating nut is arranged around the pressure stud, the upper end thereof being fixedly connected with the knob, and the lower end thereof being provided with a supporting part; the spinning press block is arranged around the floating nut, the inner side thereof abutting against the floating nut, and the outer side thereof being in thread-fit connection with an inner side of the protrusion, and the lower end thereof being supported by the supporting part, and the spinning press block is provided with a holding hole penetrating through from top to bottom; the spring is sheathed outside the floating nut, with the upper end of the spring abutting against a top inner surface of the protrusion, and the lower end of the spring abutting against the upper end of the spinning press block; the connecting piece is placed in the holding hole, and the connecting piece does not rise along with the spinning press block, but rotates with the spinning press block, and the lower end of the connecting piece is fixedly connected with the pointer; the pointer is arranged horizontally, and one end of the pointer is fixedly connected to the connecting piece and rotates with the connecting piece, and the other end of the pointer pointes to different pressure values on the dial.

When the tourniquet is in use, the knob is rotated to make the pressure stud move down and press the arm to generate pressure, and the pressure counter-acts on the floating nut to move it up, and the floating nut drives the spinning press block to rotate up and compress the spring. Since the spinning press block and the belt plate are screwed together, and the belt plate is fixed, the spinning press block performs rotation and upward movement at the same time. The pointer and the spinning press block are connected by a pin, and the pointer follows the spinning press block to rotate and point to different pressure values on the dial.

Wherein, the fixing module is used to fix the tourniquet to the part to be hemostasis of the patient; the hemostatic module is used to press the bleeding part to stop bleeding; and the indicating module is used to indicate the pressure applied to the hemostasis point.

In the second aspect of the present invention, another tourniquet is provided. The tourniquet comprises a fixing module, which includes a belt plate and a connecting belt; wherein the belt plate comprises a through hole and a protrusion formed by extending upward from circumference side of the through hole and retracting inwardly at a top end to form an annular opening, and both ends of the belt plate are respectively connected to both ends of the connecting belt which has an adjustable length; a hemostatic module, which includes a knob, a pressure stud, and a hemostatic pad; wherein the knob is wrapped around the protrusion and rotatable relative to the protrusion; the pressure stud penetrates the knob and the protrusion, and the upper part of the pressure stud is threadedly connected with the knob, and the lower end of the pressure stud is fixedly connected with the hemostatic pad, and the pressure stud threadedly matched with the knob moving downward by rotating the knob to drive the hemostatic pad to press down; wherein, the tourniquet further comprises a time device for recording duration of hemostasis.

In the third aspect of the present invention, there is provided yet another tourniquet. The tourniquet includes a fixing module, which includes a belt plate and a connecting belt; wherein the belt plate comprises a through hole, and a protrusion formed by extending upward from circumference side of the through hole and retracting inward at a top end to form an annular opening, wherein both ends of the belt plate are respectively connected to both ends of the connecting belt which has an adjustable length; a hemostatic module, which includes a knob, a pressure stud, and a hemostatic pad; wherein the knob is wrapped around the protrusion and rotatable relative to the protrusion, and the knob is provided with a time device for recording duration of hemostasis; the pressure stud is provided with an external thread, and the lower end of the pressure stud is fixedly connected with the hemostatic pad; wherein the pressure stud moves downward by rotating the knob to drive the hemostatic pad to press down; and an indication module, which includes a floating nut, a spinning press block, a spring, a connecting piece, a pointer and a dial; wherein the upper end of the floating nut is fixedly connected with the top cover of the knob, the floating nut is provided with an internal threads, wherein the floating nut penetrates the protrusion and into inner cavity of the protrusion, and the lower end of the floating nut is provided with a supporting part; wherein the pressure stud is arranged in the inner cavity of the floating nut, and is threadedly connected with the internal thread of the floating nut, wherein rotation of the knob drives the floating nut to rotate, so that the pressure stud threadedly connected with the floating nut moves downward; the spinning press block is arranged around the floating nut, with an inner side thereof abutting against the floating nut, and the outer side thereof being threaded with an inner side of the protrusion, and the lower end thereof being supported by the supporting part, the spinning press block is provided with a holding hole penetrating through from top to bottom; the spring is sleeved outside the floating nut, with the upper end of the spring abutting against a top inner surface of the protrusion, and the lower end of the spring abutting against the upper end of the spinning press block; the connecting piece is disposed in the holding hole, and the connecting piece does not rise along with the spinning press block, but rotates along with the spinning press block, and the lower end of the connecting piece is fixedly connected with the pointer; the pointer is arranged horizontally, and one end of the pointer is fixedly connected to the connecting piece and rotates with the connecting piece, and the other end of the pointer points to different pressure values on the dial.

In another preferred embodiment, the time device is arranged on the top of the knob.

In another preferred embodiment, the time device is an electronic clock. Under the condition that the tourniquet is tied to a patient and starts to stop bleeding, the electronic clock starts timing, and when the tourniquet is removed from the patient and hemostasis is stopped, the electronic clock stops timing, thus the electronic clock displays the duration of hemostasis.

In another preferred embodiment, the electronic clock includes an on-off key. When the on-off key is pressed, the timing starts, and when the on-off key is pressed again, the timing stops.

In another preferred embodiment, the electronic clock includes a sensor. When the sensor detects a human body, the sensor controls the clock to start timing, and when the sensor can not detect a human body, the sensor controls the clock to stop timing.

In another preferred embodiment, the time device is a clock paddle, which is in the shape of a ring or a disc. A time scale is marked on the clock paddle. The clock paddle is fitted in a groove of the knob and is rotatable relative to the groove. An indicator mark is further provided on the knob.

In another preferred embodiment, when the tourniquet is in use, the indicator mark corresponds to the time scale on the clock paddle to indicate the time to start hemostasis. The medical staff can estimate the patient's hemostasis time based on the current time.

In another preferred embodiment, the division value of the time scale on the clock paddle can be, but not limited to, 10 min, 15 min, 20 min, 30 min, and 60 min.

In another preferred embodiment, the clock paddle includes a positioning member for positioning the position of the clock paddle relative to the knob to limit the rotation of the clock paddle relative to the knob during hemostasis.

In another preferred embodiment, the floating nut is integrated or integrally formed.

In another preferred embodiment, the tourniquet includes a rotation locking device, which includes a ring of V-shaped grooves arranged on outer periphery of the knob, and a wedge pin loaded with a spring and fixed on one side of the belt plate.

In another preferred embodiment, when the knob is rotated in the first direction, the wedge-shaped pin automatically rebounds away from the V-shaped groove on the knob, and when the knob is rotated in the second direction, the wedge-shaped pin is engaged with the V-shaped groove, and the knob cannot be rotated. Only when the wedge-shaped pin is pulled away from the V-shaped groove, the knob can be rotated in the second direction.

In another preferred embodiment, the acute angle formed by the first side of the V-shaped groove and the tangent to the apex of the V-shaped groove is in the range of 5-45 degrees; preferably, 10-30 degrees; more preferably, 15-25 degrees.

In another preferred embodiment, the acute angle formed by the second side of the V-shaped groove and the tangent to the apex of the V-shaped groove is in the range of 45-90 degrees; preferably, 50-80 degrees; more preferably, 60-70 degrees.

In another preferred embodiment, whether the knob is rotated in the first direction or in the second direction, the wedge-shaped pin is always engaged with the V-shaped groove, and the knob cannot be rotated. Only when the wedge-shaped pin is pulled away from the V-shaped groove, the knob can be rotated in the first direction or the second direction.

In another preferred embodiment, the acute angle formed by the first side of the V-shaped groove and the tangent to the apex of the V-shaped groove and the acute angle formed by the second side of the V-shaped groove and the tangent to the apex of the V-shaped groove are both in the range of 45-90 degrees; preferably, 50-80 degrees; more preferably, 60-70 degrees.

In another preferred embodiment, the first direction is a clockwise direction or a counterclockwise direction, and the second direction is a counterclockwise direction or a clockwise direction.

In another preferred embodiment, the floating nut includes an upper part and a lower part, wherein the upper part and the lower part are detachably fixedly connected, and the upper part is not provided with threads, while the lower part is provided with internal threads that match external threads of the pressure stud.

In another preferred embodiment, the upper part and the lower part are snap-connected, wherein the lower end of the upper part is provided with lower teeth and/or lower grooves, and the upper end of the lower part is provided with upper grooves and/or the upper teeth, wherein the upper part and the lower part insert the teeth into the grooves to be engaged and fixed by axial pressure, or separate the teeth from the grooves by axial tension.

In another preferred embodiment, the lower teeth and/or the lower grooves are matched with the upper grooves and/or the upper teeth.

In another preferred embodiment, both sides of the belt plate are curved, so that an inner surface of the belt plate fits an outer surface of a hand for hemostasis.

In another preferred embodiment, both sides of the belt plate are flat.

In another preferred embodiment, the rotation angle of the pointer is in a range of 30-180 degrees.

In another preferred embodiment, the dial has a scale stroke in a range of 5-50 N.

In another preferred embodiment, the spring has a wire diameter of 0.5-1.5 mm, a height of 5-30 mm, and a screw pitch of 1-10 mm.

In another preferred embodiment, the number of the dials is 1-10.

In another preferred embodiment, the number of the pointers is multiple.

In another preferred embodiment, the hemostatic pad is transparent.

In another preferred embodiment, the material of the hemostatic pad is selected from the following group: silica gel, TPE, rubber, PU, latex and a combination thereof.

In another preferred embodiment, the tourniquet includes a fixed pad, which is used to assist in supporting the tourniquet.

In another preferred embodiment, the tourniquet includes a baffle plate, which is fixed to the bottom of the belt plate. The baffle plate and the belt plate enclose a pointer compartment, and the pointer can rotate in the pointer compartment, and the baffle plate is also used for supporting the floating nut.

In another preferred embodiment, the tourniquet includes a baffle plate, which is fixed to the bottom of the belt plate. The baffle plate and the belt plate enclose a pointer compartment, which is arc-shaped, and the pointer can rotate in the pointer compartment, and the baffle plate is also used for supporting the floating nut.

In another preferred embodiment, the pointer is a bidirectional pointer, which includes a rotating ring, a first pointer and a second pointer. Wherein, the top surface of the rotating ring is fixedly connected to the connecting member. The first pointer extends outward from the rotating ring in a radial direction of the rotating ring, and the second pointer extends from the rotating ring in a direction opposite to the first pointer.

In another preferred embodiment, the dial is arranged on the belt plate.

In another preferred embodiment, the floating nut and the pressure stud are screw-fitted connected.

In another preferred embodiment, a nominal diameter of the holding hole is larger than a nominal diameter of the connecting piece.

In another preferred embodiment, the screw threads for matching the protrusion with the spinning press block have a screw pitch of 20 mm-80 mm.

In another preferred embodiment, the connecting member is a rod with higher strength, such as a pin.

In another preferred embodiment, the outer surface of the connecting member is a smooth surface.

In another preferred embodiment, the inner surface of the holding hole is a smooth surface.

In another preferred embodiment, the upper end of the connecting member abuts against the top surface of the protrusion.

In another preferred embodiment, one end of the connecting belt is fixedly connected to one end of the strap plate, and the other end of the connecting belt is detachably connected to the other end of the strap plate.

In another preferred embodiment, the adjustable connecting structure includes a side hole. A belt with single hooks on the surface is provided on the movable end of the connecting belt, and the connecting belt is made of plush material. The movable end of the connecting belt passes through the side hole, and is fixedly glued to the main body of the connecting belt by the belt with single hooks on the surface.

In another preferred embodiment, the adjustable or flexible connecting structure includes a connecting belt fixed on the side holes on both sides and its hook and loop fasteners. The hook and loop fastener on the connecting belt at one end is with a hook surface, and the other end is with a wool surface. The two types of hook and loop fasteners can be pressed and fixed.

In another preferred embodiment, the strap plate includes four-sided long holes, and the four connecting belts are respectively fixed through the long holes.

In another preferred embodiment, the connecting belt is made of medical tape, wherein the outer end of the connecting belt is a glue surface, which can be firmly attached to human skin or another connecting belt.

In another preferred embodiment, one end of the connecting belt is fixed to one side hole, and a buckle is provided near the side hole, and the other end is inserted into the other side hole and then folded back into the buckle for fixing.

In another preferred embodiment, the pointer is a bidirectional pointer.

In another preferred embodiment, the bidirectional pointer includes a rotating ring, a first pointer and a second pointer. The top surface of the rotating ring is fixedly connected to the connecting member. The first pointer extends outward from the rotating ring in a radial direction of the rotating ring, and the second pointer extends from the rotating ring in a direction opposite to the first pointer.

In another preferred embodiment, the bidirectional pointer is integrated or integrally formed.

In another preferred embodiment, the first pointer and the second pointer respectively correspond to a dial, and the two dials make it easier for the doctor to observe the magnitude of the applied force.

In another preferred embodiment, the pressure stud is a hollow structure which forms a visible channel, so that an operator can clearly observe a bleeding at a puncture point through the visible channel.

In another preferred embodiment, a portion of a top cover of the knob corresponding to a hollow cavity of the pressure stud is provided with a central through hole, which is a part of the visible channel.

In another preferred embodiment, the diameter of the inner cavity of the pressure stud is 5-30 mm, preferably 20 mm.

In another preferred embodiment, a bottom surface of the pressure stud and the hemostatic pad are transparent.

In another preferred embodiment, the pressure stud is opaque, and one or more through holes are opened on the bottom surface of the pressure stud, and the bleeding at the puncture point can be observed through the one or more through holes.

In another preferred embodiment, the unit of the pressure value on the dial may also be Kpa, mmHg, etc.

It should be understood that, within the scope of the present invention, the above-mentioned technical features of the present invention and the technical features specifically described in the following (such as the embodiments) can be combined with each other to form a new or preferred technical solution. Due to space limitations, they are not repeated one by one again.

EXPLANATORY NOTES OF DRAWINGS

In order to describe the technical solutions in the embodiments of the present invention or in the prior art more clearly, the following will briefly introduce the drawings that need to be used in the description of the embodiments or the prior art. Obviously, the drawings in the following description are only some embodiments of the present invention. For those of ordinary skill in the art, other drawings can be obtained based on these drawings without creative work.

Figure 1:
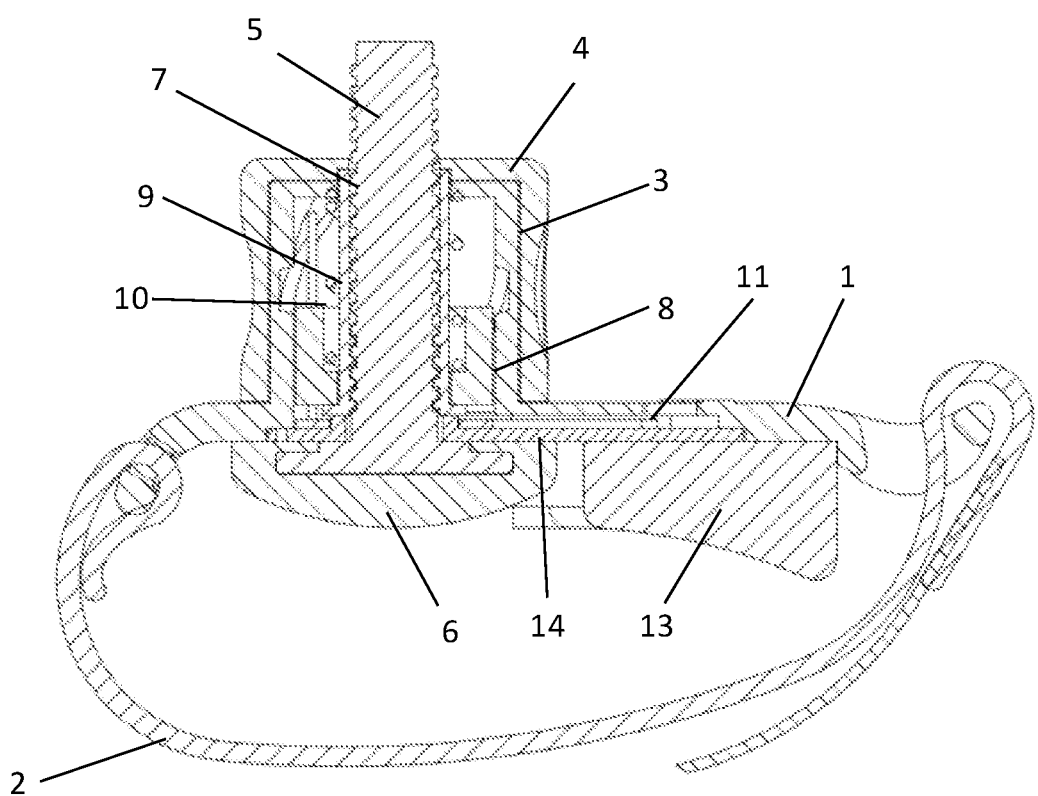
FIG. 1 is a cross-sectional view of a tourniquet in an example of the present invention.
Figure 2:
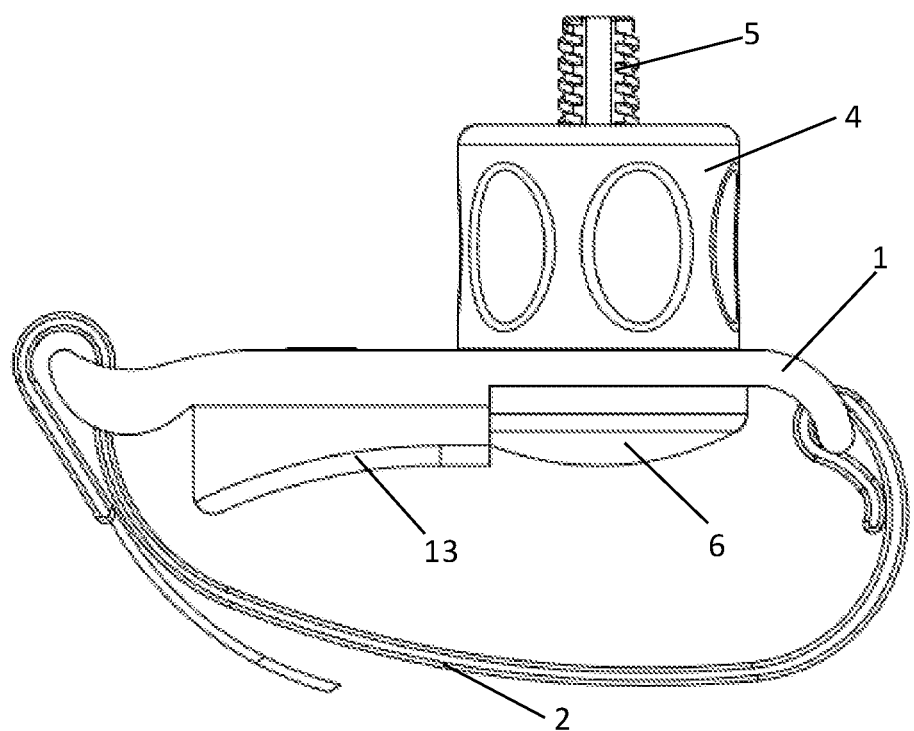
FIG. 2 is a front view of a tourniquet in an example of the present invention.
Figure 3:
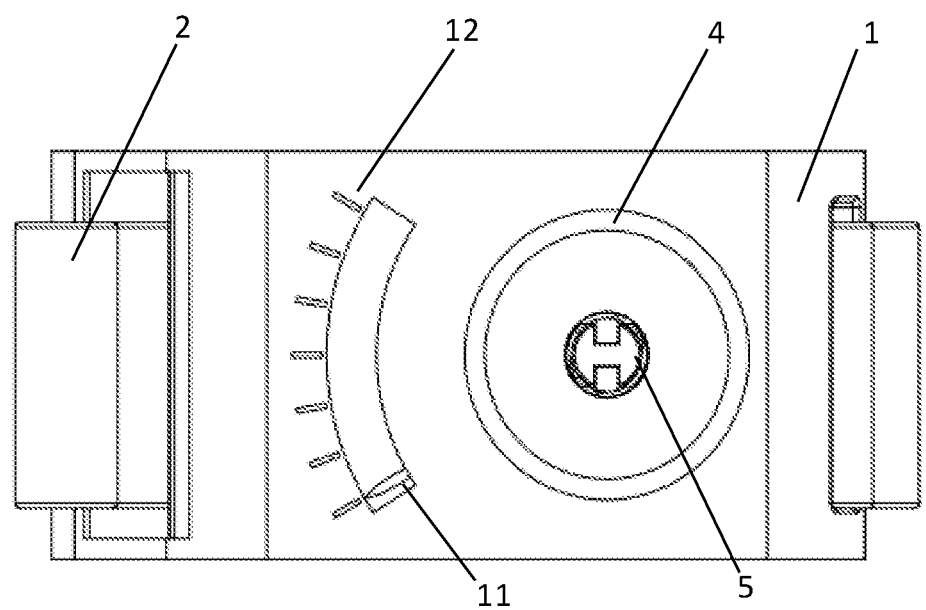
FIG. 3 is a top view of a tourniquet in an example of the present invention.
Figure 4:
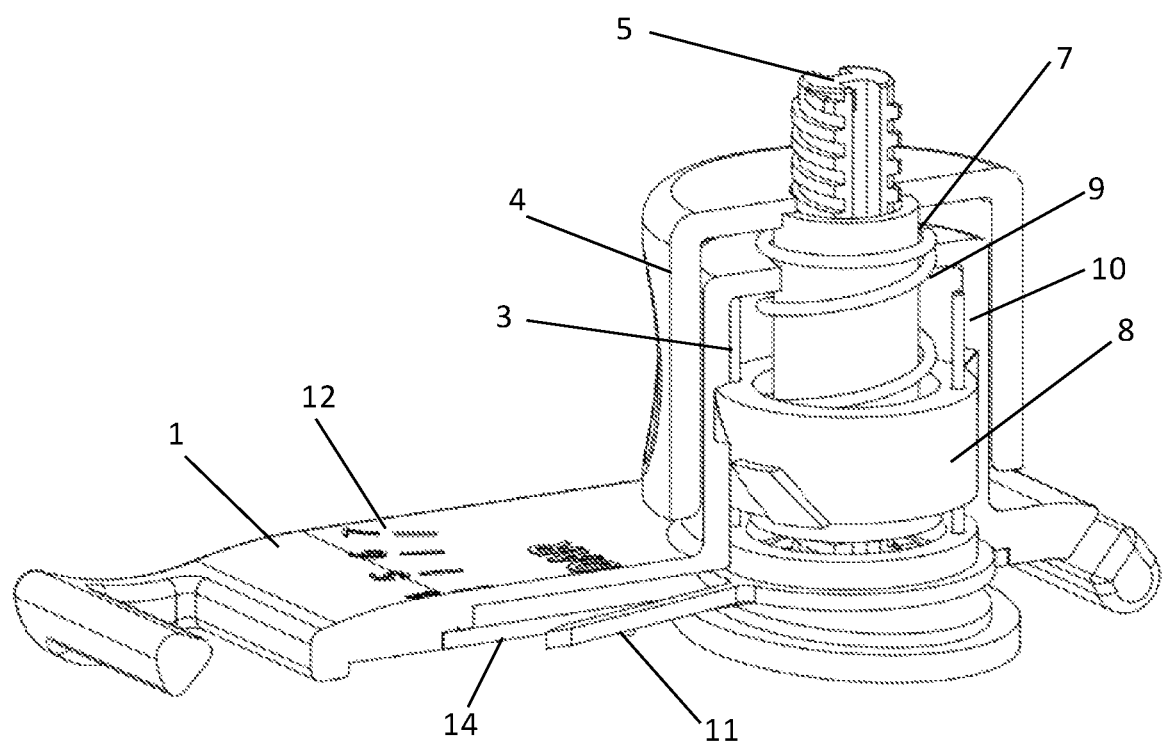
FIG. 4 is a partial cross-sectional view of a tourniquet in an example of the present invention.
Figure 5:
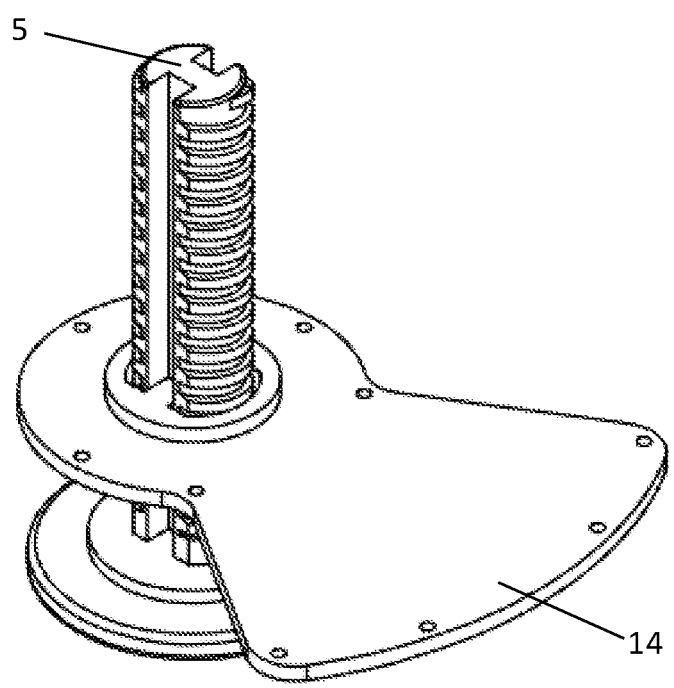
FIG. 5 is a perspective view of the assembled pressure stud and baffle plate in an example of the present invention.
Figure 6:
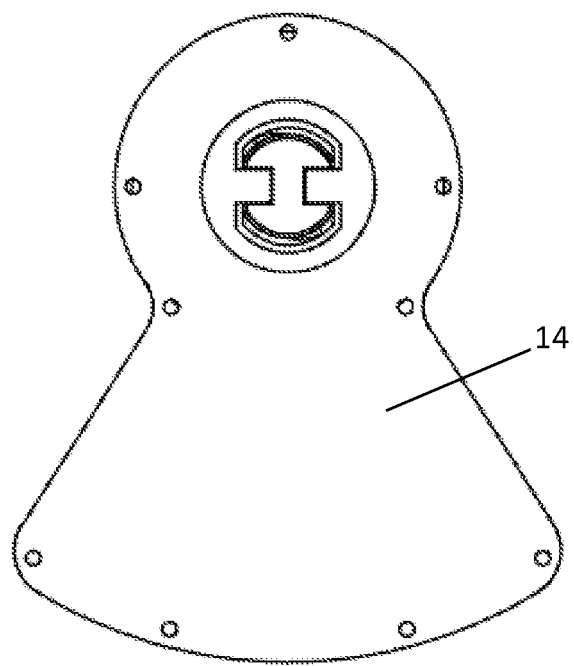
FIG. 6 is a front view of the baffle plate in an example of the present invention.
Figure 7:
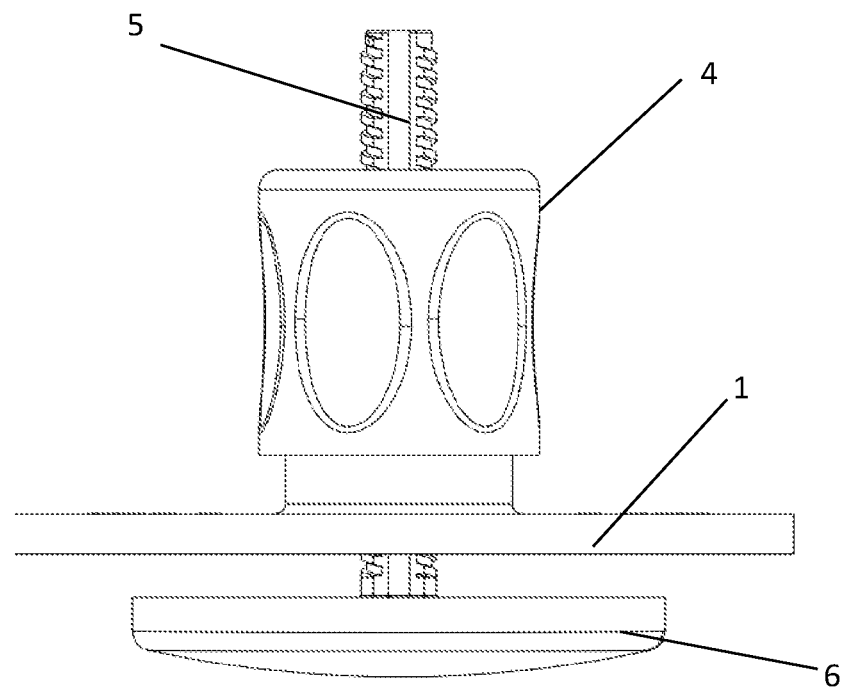
FIG. 7 is a front view of a tourniquet in another example of the present invention.
Figure 8:
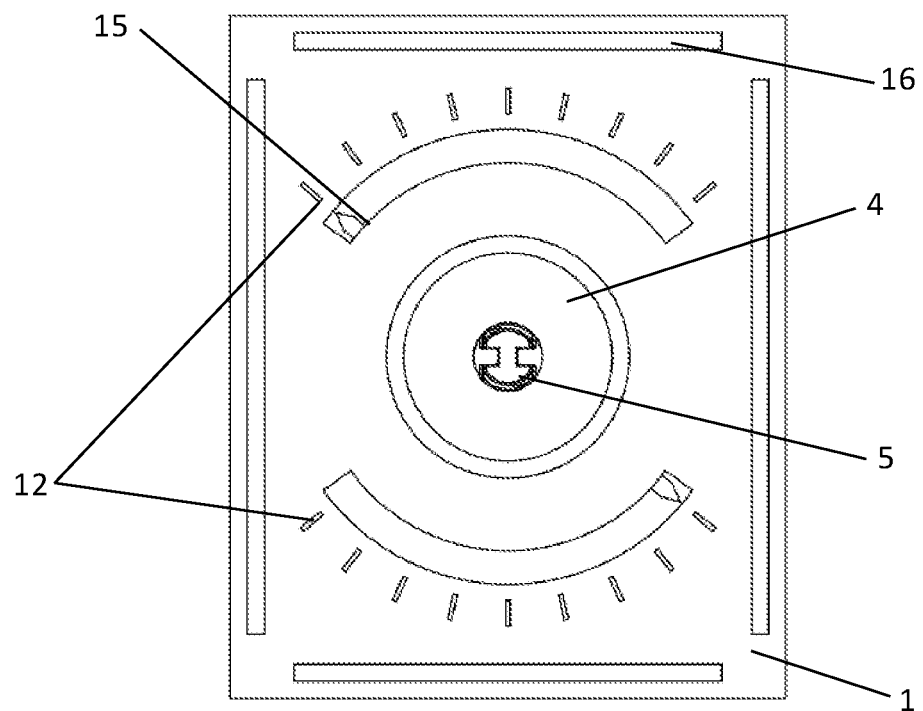
FIG. 8 is a top view of a tourniquet in another example of the present invention.
Figure 9:
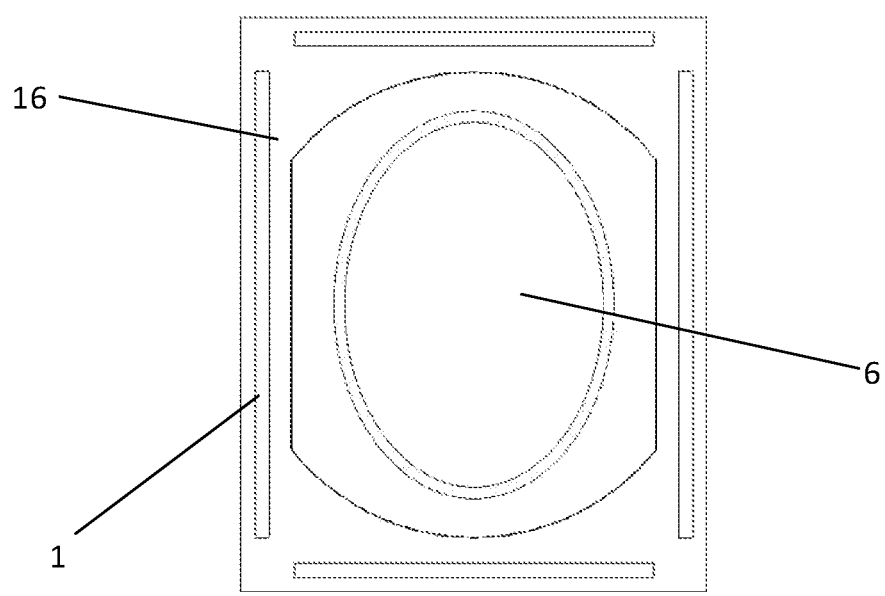
FIG. 9 is a bottom view of a tourniquet in another example of the present invention.
Figure 10:
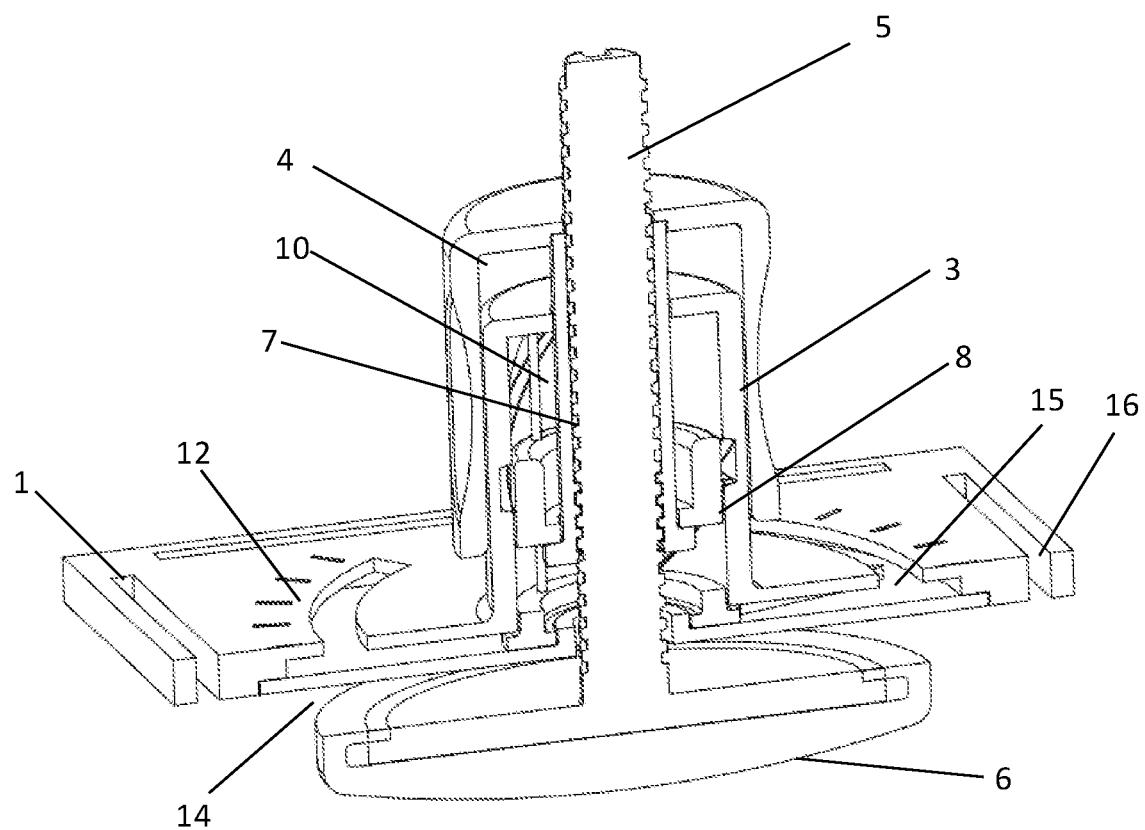
FIG. 10 is a cross-sectional view of a tourniquet in another example of the present invention.
Figure 11:
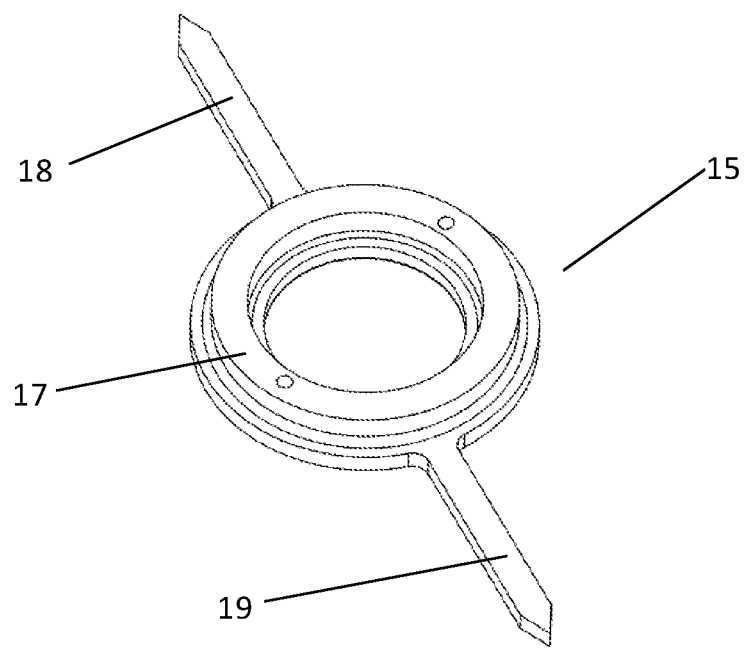
FIG. 11 is a perspective view of a pointer in another example of the present invention.
Figure 12:
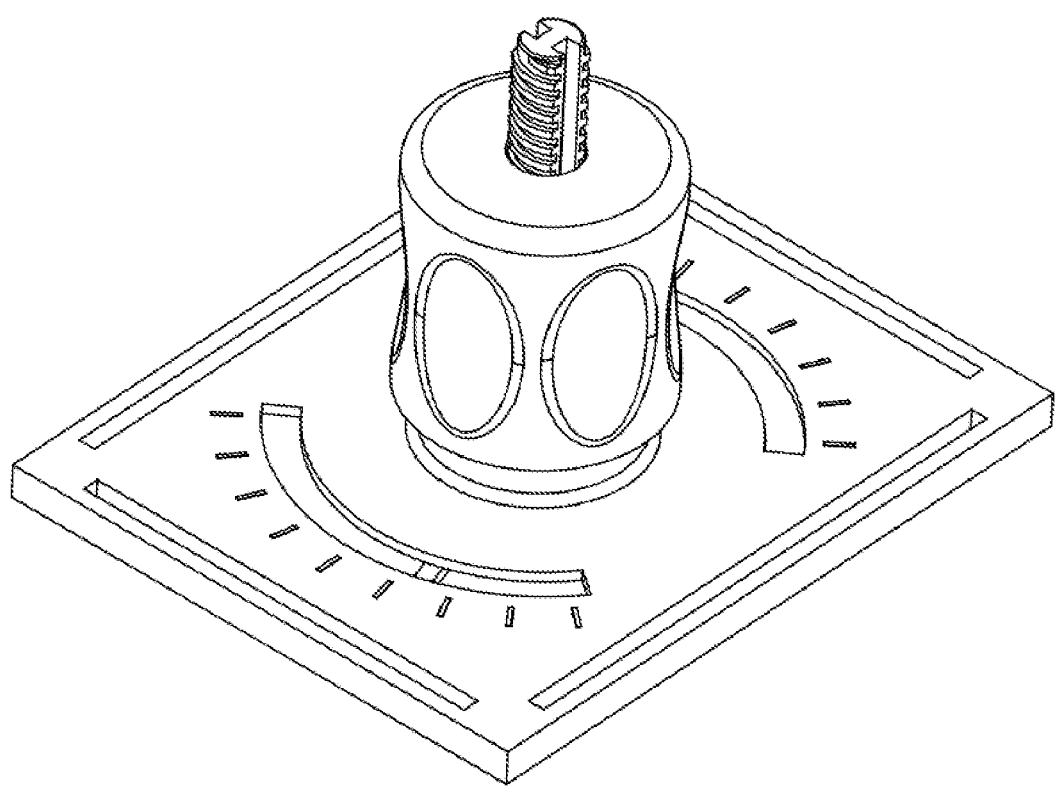
FIG. 12 is a perspective view of a tourniquet in another example of the present invention.
Figure 13:
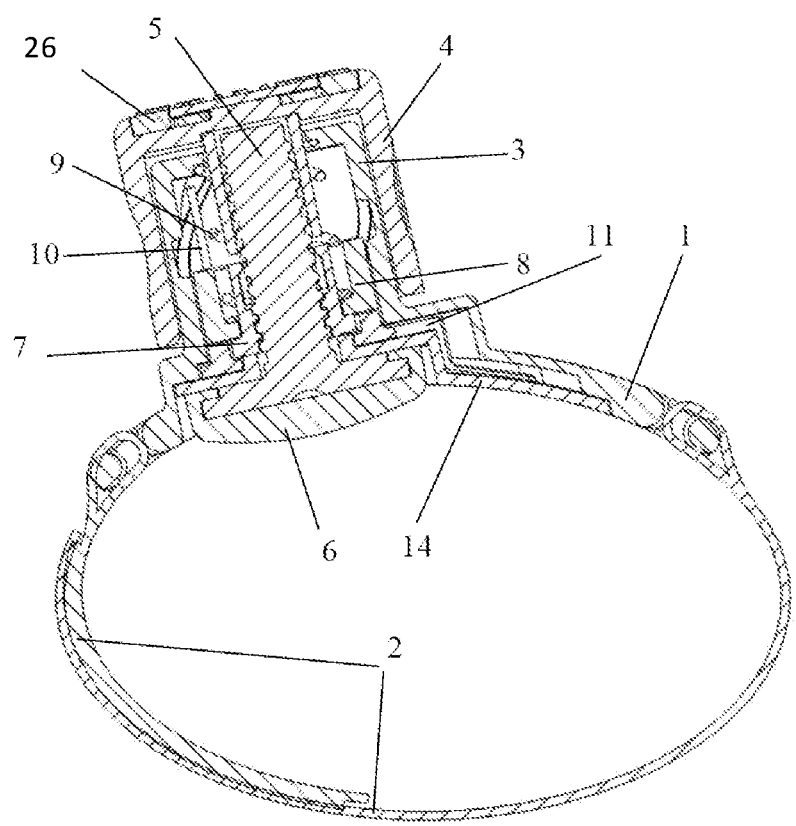
FIG. 13 is a cross-sectional view of a tourniquet in yet another example of the present invention.
Figure 14:
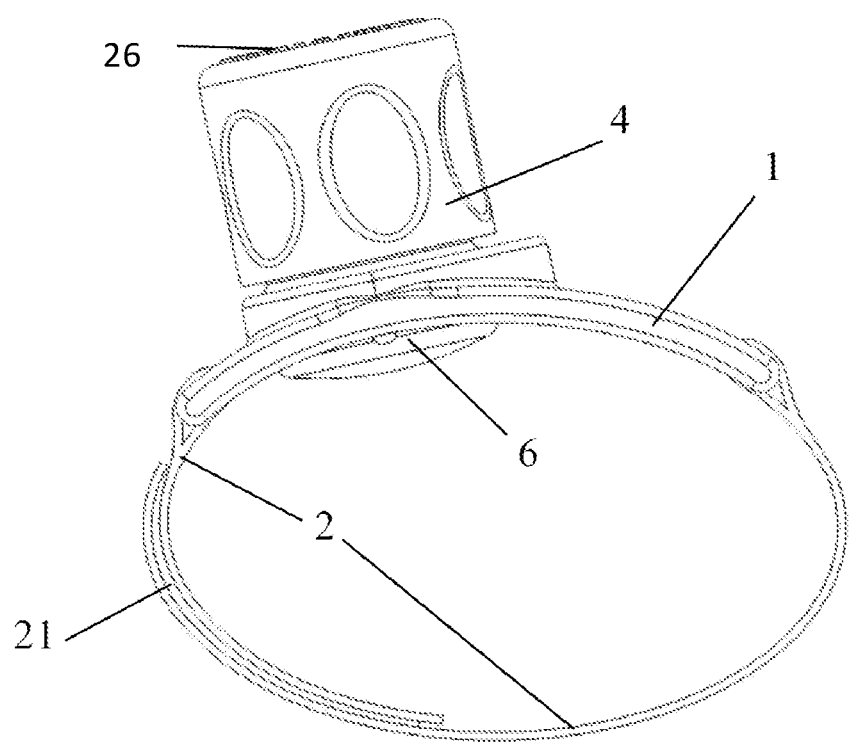
FIG. 14 is a front view of a tourniquet in yet another example of the present invention.
Figure 15:
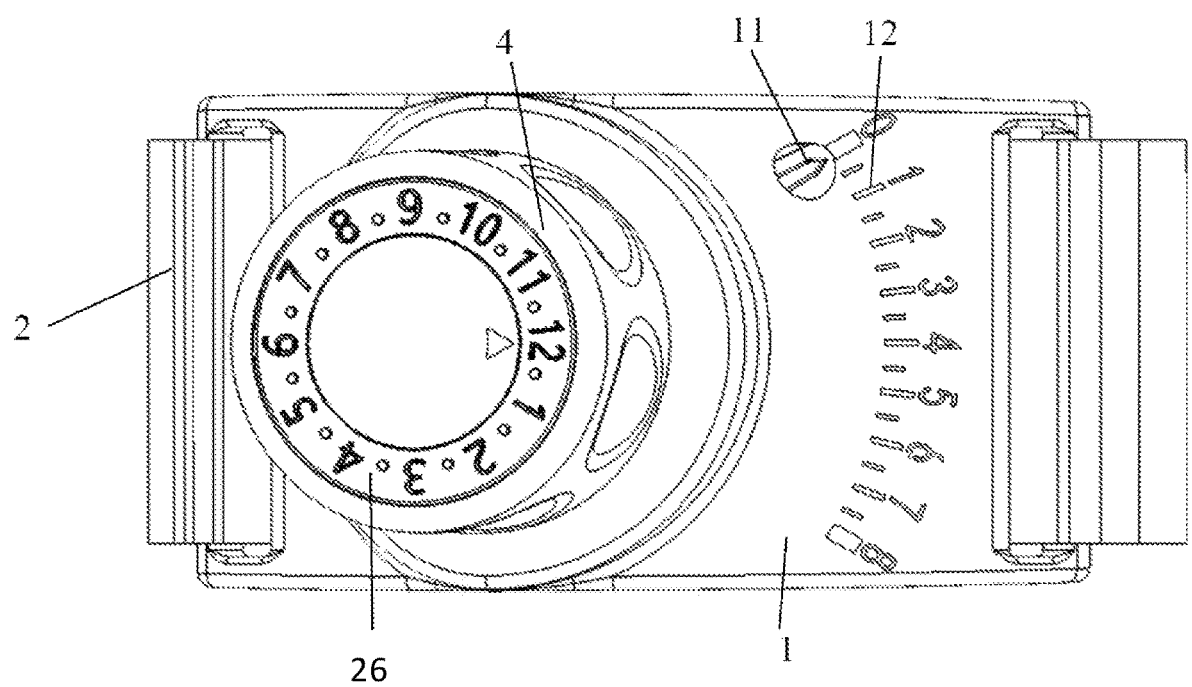
FIG. 15 is a top view of a tourniquet in yet another example of the present invention.
Figure 16:
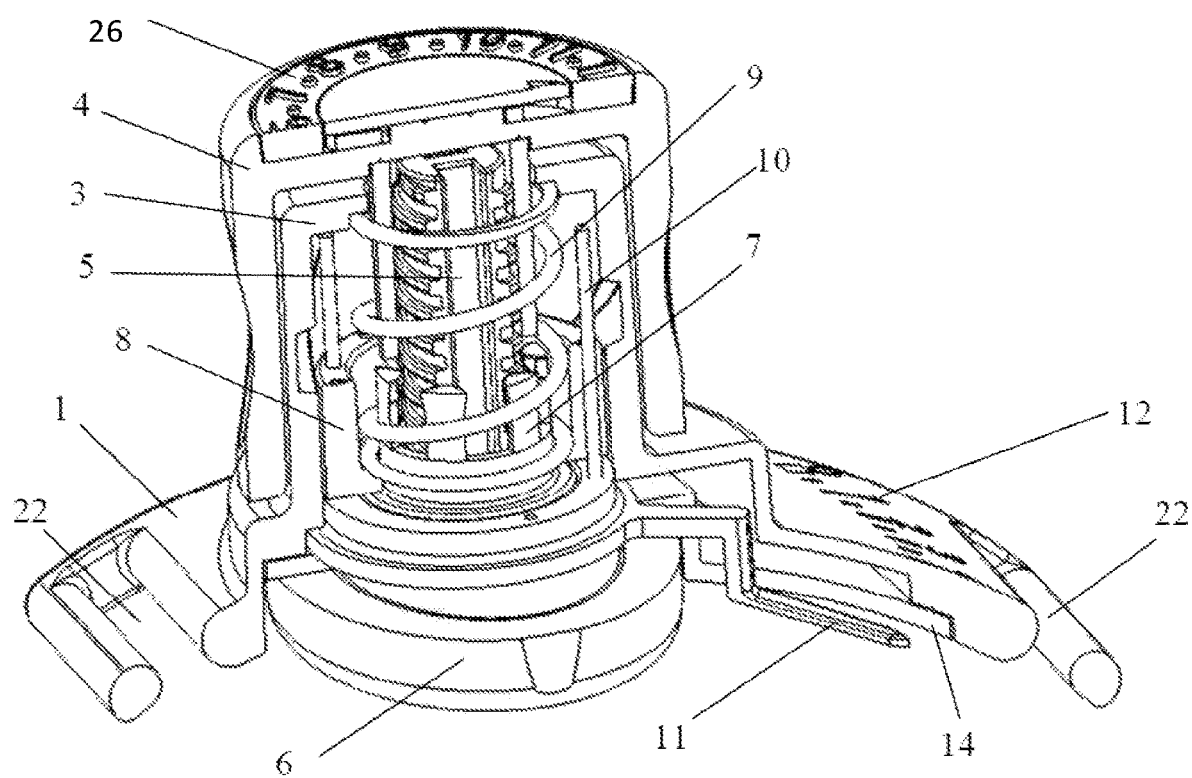
FIG. 16 is a partial cross-sectional view of a tourniquet in yet another example of the present invention.

In the drawings, the labels are as follows:
1—Belt plate;
2—Connecting belt;
3—Protrusion;
4—Knob;
5—Pressure stud;
6—Hemostatic pad;
7—Floating nut;
8—Spinning block;
9—Spring;
10—Pin;
11—Pointer;
12—Dial;
13—Fixed pad;
14—Baffle plate;
15—Bidirectional pointer;
16—Long hole;
17—Rotating circle;
18—First pointer;
19—Second pointer;
20—Buckle;
21—Velcro tape;
22—Side hole;
23—Wedge pin;
24—V-shaped groove;
25—Wedge pin holder;
26—Clock paddle;
27—Upper part;
28—Lower part;
29—Center through hole.

SPECIFIC EMBODIMENTS

After extensive and intensive researches, the inventors have developed a tourniquet for the first time through a large number of screenings. Compared with the prior art, the tourniquet of the present invention drives the pointer to rotate through the threaded cooperation between the components, which shows the pressure value applied by the doctor. The present invention is simpler in structure, easy to process, convenient to observe the pressure value applied by the doctor, accurate display, and convenient adjustment. The present invention has been completed on this basis.

The invention provides a tourniquet, which is a tourniquet with a specific structure, and is particularly suitable for hemostasis at a puncture point after interventional operation through radial artery or femoral artery. Typically, the floating nut and the pressure stud of the tourniquet of the present invention are matched by threads. The pressure stud can only move up and down through the restraining mechanism. The knob and the floating nut are fixedly connected. Rotating the knob drives the floating nut so that the pressure stud presses the bleeding point. At this time, the floating nut produces upward displacement under pressure to drive the spinning press block to compress the spring to generate pressure. Meanwhile, the spinning press block produces a rotational movement, and this drives the pointer through the connecting piece, so that the spring compression displacement and the pointer deflection angle are synchronized. That is, the spring compression distance and the pointer deflection angle are synchronized. According to the spring force formula $F=K*L$ (K is the spring force coefficient, L is the spring compression length), the spring force is proportional to the pointer deflection angle. According to the force synthesis rule, the elastic force of the spring is decomposed into the downward thrust and rotational force of the spinning press block, wherein the downward thrust is the pressure of the hemostatic pad. It can be concluded that the pressing force of the hemostatic pad is positively correlated with the deflection angle of the pointer, and the pressing force can be marked on the dial of the belt plate through the detection and setting of the detector to show the actual pressure of the hemostatic pad.

When in use, the hemostatic pad of the present invention is aligned with the bleeding position of the radial artery or femoral artery, and then the connecting belt is tightened, and then the knob is rotated to push the pressure stud to compress the bleeding point, and at the same time, the pressure on the bleeding point is displayed by the pointer.

In another preferred embodiment, the outer surface of the knob is provided with patterns and/or grooves to facilitate the user to rotate the knob.

In another preferred embodiment, the cross section of the pressure stud is ⊤-shaped.

In another preferred embodiment, the baffle plate is matched with the ⊥-shaped section of the pressure stud to fix the pressure stud without displacement.

The main advantages of the present invention include:
(a) The tourniquet of the present invention has a simple structure and is easy to process and produce;
(b) The pressure can be accurately displayed through the pointer and scale, so as to achieve the purpose of precise control of the pressure, and the pointer and scale are set horizontally, which is more convenient for observation and convenient for clinical operation;
(c) On the basis of adjusting the compression strength, a spring is added to buffer the pressure, which gives the patient a certain degree of mobility and makes it have a good hemostatic effect;
(d) The design mode of tightening the connecting belt with a buckle makes the clinical operation more convenient;
(e) Non-medical personnel cannot adjust the pressure privately by setting a rotating locking device or by the split design of the floating nut to avoid the risk of bleeding;
(f) It is convenient for medical staff to measure the hemostasis time by setting up a time device.

Therefore, through the tourniquet of the present invention, medical personnel can independently adjust the pressure to stop bleeding according to the actual situation of the patient, provide the patient with a stable hemostasis pressure, greatly improve the success rate of the patient's hemostasis, and the pressure is visible, which is convenient for adjusting the force during the process. The control also reduces the labor intensity of medical staff, is convenient to operate, stable and reliable, and improves safety.

The present invention will be further explained below in conjunction with specific embodiments. It should be understood that these embodiments are only used to illustrate the present invention and not to limit the scope of the present invention. In addition, the drawings are schematic diagrams, so the device and equipment of the present invention are not limited by the size or ratio of the schematic diagrams.

It should be noted that in the claims and specification of this patent, relational terms such as first and second are only used to distinguish one entity or operation from another entity or operation, and do not necessarily require or imply any such actual relationship or order between these entities or operations. Moreover, the terms "include", "comprise" or any other variants thereof are intended to cover non-exclusive inclusion, so that a process, method, article, or device including a series of elements includes not only those elements, but also other elements not explicitly listed, or elements inherent to the process, method, article, or equipment. If there are no more restrictions, the element defined by the sentence "including a/an" does not exclude the existence of other same elements in the process, method, article, or equipment including the element.

Example 1

The tourniquet of this embodiment is shown in FIGS. 1-6. The tourniquet of this embodiment includes a fixing module, a hemostatic module and an indicating module. The tourniquet of this embodiment is used for radial artery Internationale surgery.

The fixed module includes a belt plate 1 and a connecting belt 2. The belt plate 1 is a flat plate. One side of the belt plate 1 is provided with a through hole, and the protrusion 3 is formed by extending upward from the circumferential side of the through hole and forming an annular opening at the top end inwardly. Both ends of the belt plate 1 are respectively provided with a first side hole and a second side hole, wherein the first side hole is fixedly connected to one end of the connecting belt 2, and the other end of the connecting belt 2 is provided with a belt with single hooks on the surface, which passes through the second side hole and is fixedly connected to the belt body of the connecting belt 2. The connecting belt 2 is made of plush material, and the length of the connecting belt 2 can be adjusted. In another embodiment, both ends of the belt plate 1 are respectively provided with side holes 22, and each side hole 22 is fixed with a connecting belt 2. One of the connecting belts 2 is fixed with a hair surface hook-and-loop fastener 21, and the other is fixed with a hook surface hook-and-loop fastener 21, and the two hook and loop fasteners 21 are fixed by pressing.

The hemostatic module includes a knob 4, a pressure stud 5 and a hemostatic pad 6. The knob 4 covers the protrusion 3 and is rotatable relative to the protrusion 3. The pressure stud 5 penetrates the knob 4 and the protrusion 3, and the upper part of the pressure stud 5 is threadedly connected with the knob 4, and the lower end of the pressure stud 5 is fixedly connected with the hemostatic pad 6, and the pressure stud 5 screwed with the knob 4 moves downward by rotating the knob 4 to drive the hemostatic pad 6 to press down. The hemostatic pad 6 is transparent. The material of the hemostatic pad 6 is selected from the following group: silica gel, TPE, rubber, PU, latex and a combination thereof.

The indicating module includes a floating nut 7, a spinning press block 8, a spring 9, a pin 10, a pointer 11 and a dial 12. The floating nut 7 is arranged around the pressure stud 5, and is connected with the pressure stud 5 in a threaded fit, with the upper end of the floating nut 7 being fixedly connected to a knob 4, and the lower end of the floating nut 7 being provided with a support part. The spinning press block 8 is arranged around the floating nut 7, with an inner side of the spinning press block abutting against the floating nut 7, an outer side of the spinning press block being in thread-fit connection with an inner side of a protrusion 3, and the lower end of the spinning press block being supported by the support part; the spinning press block 8 is provided with a holding hole penetrating through from top to bottom. The screw pitch of the screw thread matching the protrusion 3 with the spinning press block 8 is in a range of 20 mm-80 mm. The spring 9 is sheathed outside the floating nut 7, with the upper end of the spring 9 abutting against the top face of the protrusion 3, and the lower end thereof abutting against the upper end of the spinning press block 8. The wire diameter 9 of the spring is 0.5-1.5 mm, the height is 5-30 mm, and the screw pitch is 1-10 mm.

The pin 10 is placed in the holding hole, and the diameter of the holding hole is larger than the diameter of the pin 10. The pin 10 does not rise with the spinning press block 8 but only rotates with the spinning press block 8. The lower end of the pin 10 is fixedly connected with the pointer 11. The pointer 11 is arranged horizontally. One end of the pointer 11 is fixedly connected to the pin 10 and rotating with the pin 10, and the other end of the pointer 11 points to different pressure values on the dial 12. The dial 12 is provided on the belt plate 1. The rotation angle of the pointer 11 is in a range of 30-180 degrees. The scale stroke of the dial 12 is in a range of 5-50N.

The tourniquet includes a baffle plate 14, which is fixed at the bottom of the belt plate 1. The baffle plate 14 and the belt plate 1 enclose a pointer 11 compartment. The pointer 11 rotates in the pointer 11 compartment. The baffle plate 14 is also used to support the floating nut 7.

When the tourniquet is in use, the knob 4 is rotated to make the pressure stud 5 move down and press the arm to generate pressure, the pressure counter-acts on the floating nut 7 to move it up, and the floating nut 7 drives the spinning press block 8 to rotate up and compress the spring 9. Since the spinning press block 8 and the belt plate 1 are screwed together, and the belt plate 1 is fixed, the spinning press block 8 performs rotation and upward movement at the same time. The pointer 11 and the spinning press block 8 are connected by a pin 10, and the pointer 11 follows the spinning press block 8 to rotate and point to different pressure values on the dial 12.

The tourniquet also includes a fixed pad 13, which is used to assist in supporting the tourniquet.

Example 2

The tourniquet of this Example is substantially the same as that of Example 1, and the difference is that the pointer of the tourniquet of this Example is a bidirectional pointer, as shown in FIGS. 7-12. The bidirectional pointer includes a rotating ring 17, a first pointer 18, and a second pointer 19. Wherein, the top surface of the rotating ring 17 is fixedly connected to the pin 10. The first pointer 18 extends outward from the rotating ring 17 in the radial direction of the rotating ring 17. The second pointer 19 extends from the rotating ring 17 in a direction opposite to the first pointer 18. The rotating ring 17, the first pointer 18 and the second pointer 19 are integral or integrally formed. The first pointer 18 and the second pointer 19 respectively correspond to a dial 12. The provision of two dials 12 makes it easier for the physician to observe the magnitude of the applied force. The tourniquet in this embodiment may not be provided with a fixed pad.

In addition, the tourniquet in this embodiment is used for femoral artery Internationale surgery, and the tourniquet is tied to the patient's thigh. The belt plate 1 of the tourniquet includes four-sided long holes 16, and four connecting belts (not shown) are respectively fixed through the long holes 16. The connecting belt is made of medical tape, wherein the outer end of the connecting belt is a glue surface, which can be firmly attached to human skin or another connecting belt.

Example 3

The tourniquet of this Example is substantially the same as that of Example 1. The difference is that the top of the knob of the tourniquet of this Example is provided with a timing device, and the belt plate of the tourniquet is curved, as shown in FIGS. 13-20. A timing device is added to the tourniquet in this Example compared with Example 1, thus the upper structure of the tourniquet has also been adjusted appropriately: The upper end of the floating nut 7 is fixedly connected to the top cover of the knob 4. The floating nut 7 is provided with internal threads. The floating nut 7 penetrates the protrusion 3 and penetrates into the inner cavity of the protrusion 3. The lower end of the floating nut 7 is provided with a supporting part. The pressure stud 5 is provided with external threads, wherein the pressure stud 5 is arranged in the inner cavity of the floating nut 7 and is threadedly connected with the internal threads of the floating nut 7. The lower end of the pressure stud 5 is fixedly connected with the hemostatic pad 6. The knob 4 drives the floating nut 7 to rotate, and the pressure stud 5 connected with the floating nut 7 by threads moves downward to drive the hemostatic pad 6 to press down.

In this example, the time device is a clock paddle 26. The clock paddle 26 is ring-shaped, and the top cover of the knob 4 is provided with a groove, and the ring-shaped clock paddle 26 is fitted into the groove of the knob 4 and is rotatable relative to the groove. In one example, the time scale is marked on the clock paddle 26. The time scale in this Example is 30 min, and it can be 10 min, 15 min, 20 min, 60 min, etc. The division value can be marked on the clock paddle 26 in a form similar to a clock scale. The knob 4 is also provided with indicator mark(s). In another example, the time scale is circumferentially arranged on the knob 4, and the indicator mark is arranged on the clock paddle 26. When the tourniquet is in use, the indicator mark corresponds to the time scale on the clock paddle 26 to indicate the time to start hemostasis. The medical staff can estimate the patient's hemostasis time based on the current time.

In another preferred example, the clock paddle 26 may further include a positioning member for positioning the position of the clock paddle 26 relative to the knob 4 to limit the rotation of the clock paddle 26 relative to the knob during hemostasis. The positioning member can be a snap-fitting member. For example, one end of the snap-fitting member is hinged or pin-connected to the knob 4, and the time scale of the clock paddle 26 is designed as a depression, and the clock paddle 26 is positioned by sinking the other end of the snap-fitting member into the depression. Other examples capable of realizing the above functions are also included in the scope of the present invention. In another preferred example, the snap-fitting member and the indicator mark can be combined into one component.

Figure 17:
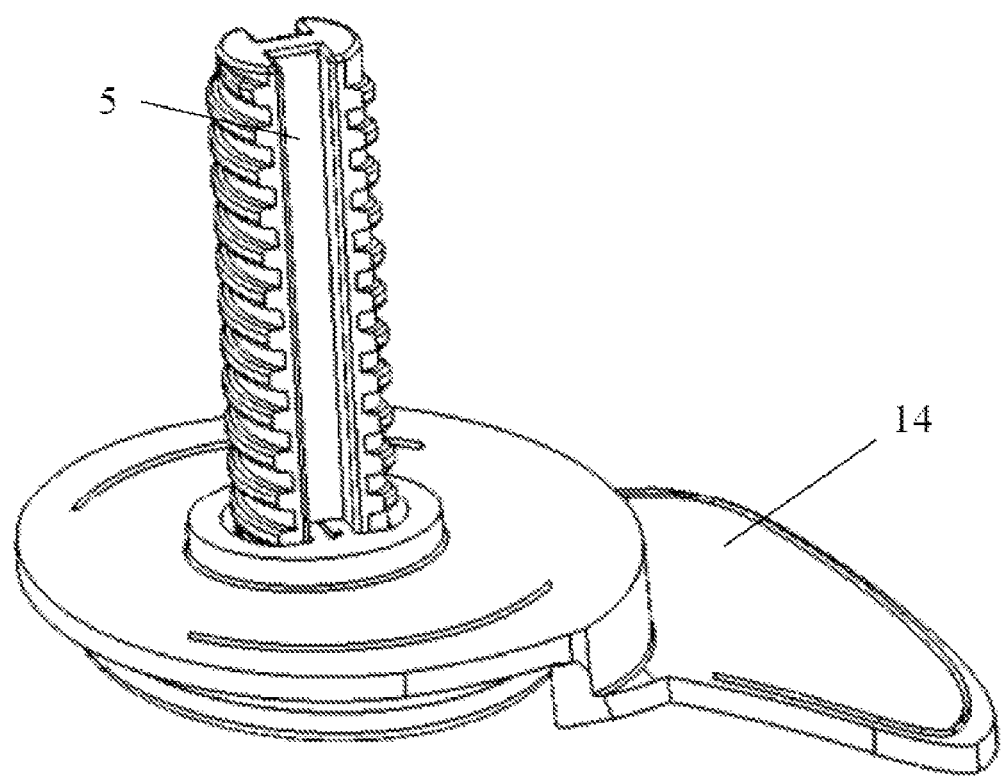
FIG. 17 is a perspective view of the assembled pressure stud and baffle plate in yet another example of the present invention.
Figure 18:
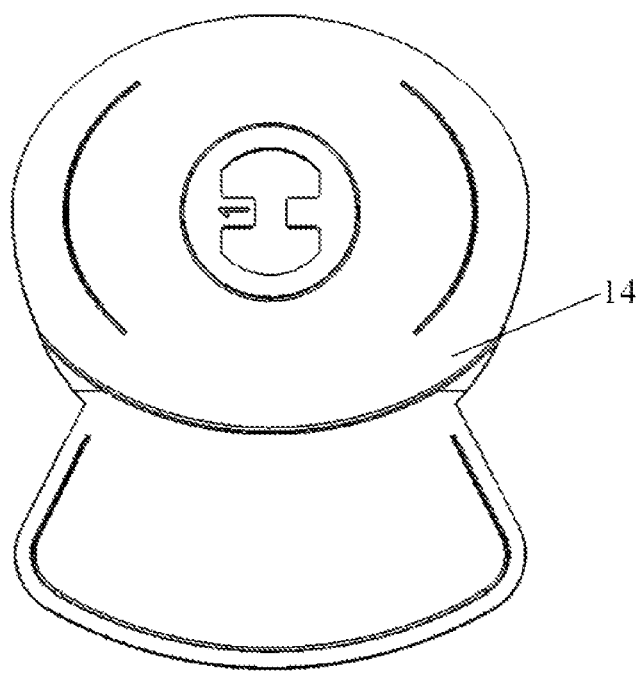
FIG. 18 is a front view of a baffle plate in yet another example of the present invention.
Figure 19:
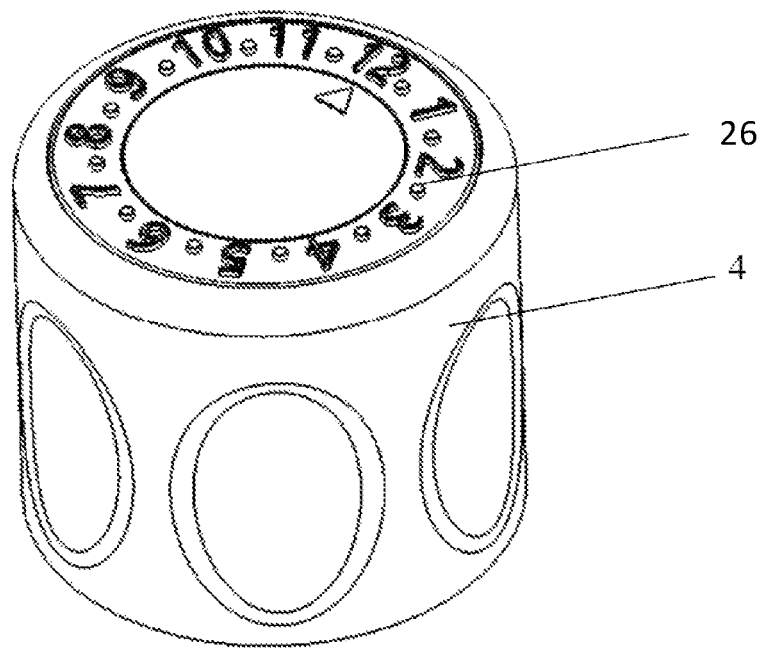
FIG. 19 is a perspective view of a knob provided with a time device in yet another example of the present invention.

Both sides of the belt plate 1 are curved. In order to cooperate with the curved shape of the belt plate 1, as shown in FIGS. 17-18, the pointer compartment enclosed by the baffle plate 14 and the belt plate 1 is also shaped into an arc shape, and the pointer 15 is also shaped into an arc shape to rotate in the pointer compartment. This design enables the tourniquet 1 to have a good fit with the human body without the fixed pad 13 and simplifies the structure of the tourniquet.

Figure 20:
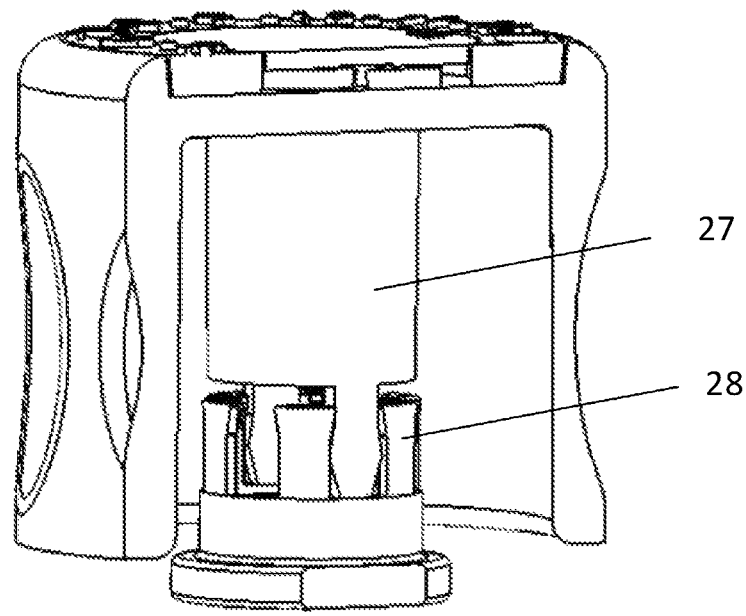
FIG. 20 is a perspective view of a floating nut fixedly connected to a knob in yet another example of the present invention, wherein the floating nut is formed by engaging the upper part and the lower part.

In addition, as shown in FIG. 20, the floating nut 7 in this example is a split design, that is, the floating nut 7 includes an upper part 27 and a lower part 28, which are detachably connected. The upper part 27 has a smooth inner surface, and the lower part 28 is provided with an internal thread that matches the external thread of the pressure stud. The upper part 27 and the lower part 28 are snap-connected. The lower end of the upper part 27 is provided with lower teeth and lower grooves in the circumferential direction, and the upper end of the lower part 28 is provided with upper grooves and upper teeth in the circumferential direction. Wherein, the teeth can be inserted into the grooves and will not easily come off. The upper part 27 and the lower part 28 engage and fix the teeth in the grooves by axial pressure, and pull the teeth out of the grooves for separation by axial tension. In use, after the tourniquet is adjusted, the time point at which hemostasis is started is recorded by the time device, and then the upper part 27 of the floating nut is separated from the lower part 28 by pulling the knob with tension. In this case, non-medical personnel cannot adjust the pressure privately to avoid the risk of bleeding.

Example 4

Figure 21:
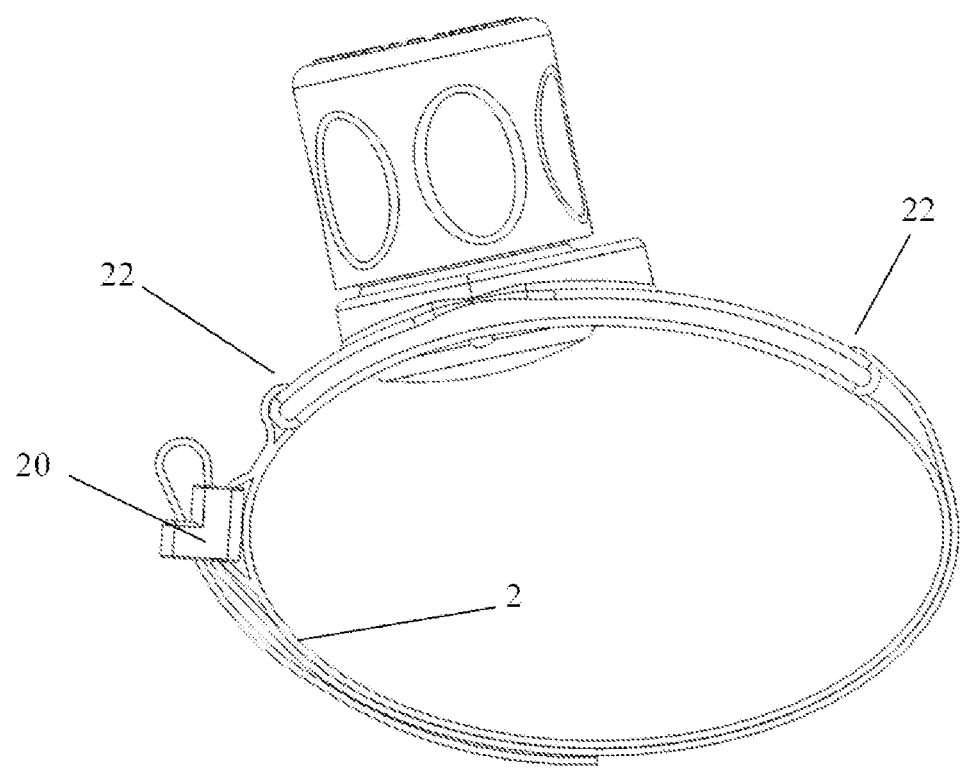
FIG. 21 is a front view of a tourniquet with a connection band secured by a buckle in another example of the present invention.

The tourniquet of this Example is substantially the same as that of Example 3. The difference is that the connecting belt 2 of the tourniquet of this Example is a smooth bandage, whose material is PVC, and it is fixed in the hole 22 on the side of the belt plate 1, and a buckle 20 is arranged near this side. The connecting belt 2 first passes through the hole 22 on the other side of the belt plate 1, and then tightens and folds back to penetrate the buckle 20 for fixing, as shown in FIG. 21.

Example 5

Figure 22:
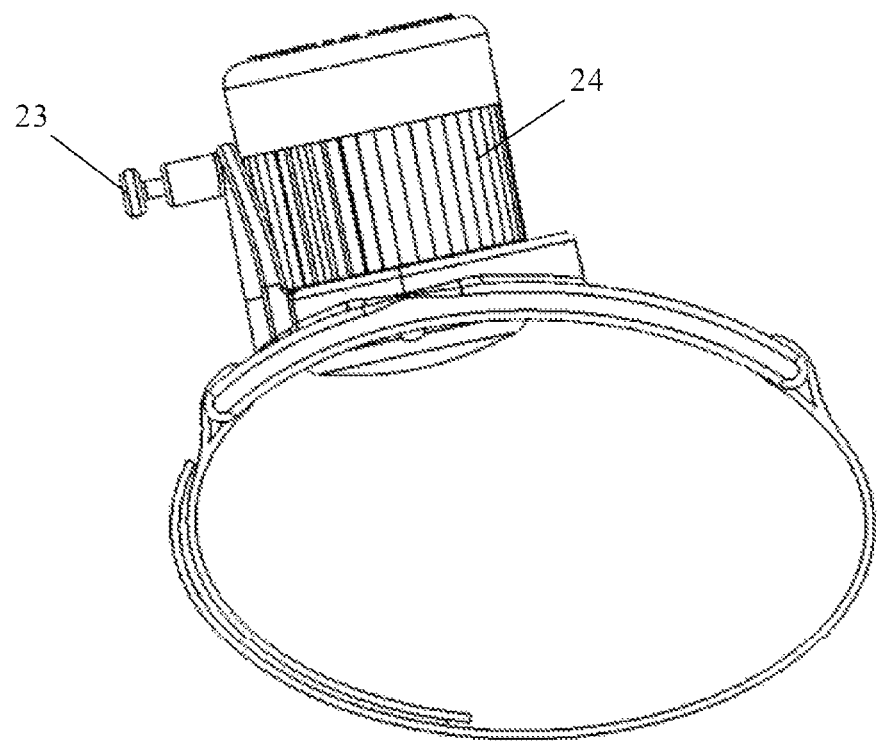
FIG. 22 is a front view of a tourniquet equipped with a rotation locking device in an example of the present invention.
Figure 23:
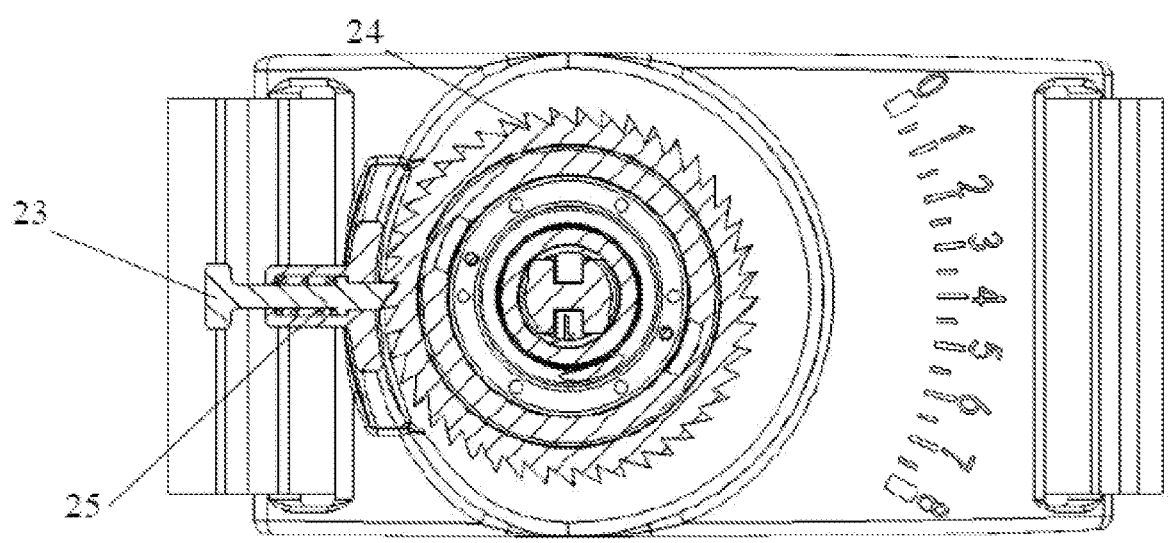
FIG. 23 is a cross-sectional view of the tourniquet provided with a rotation locking device in FIG. 22.
Figure 24:
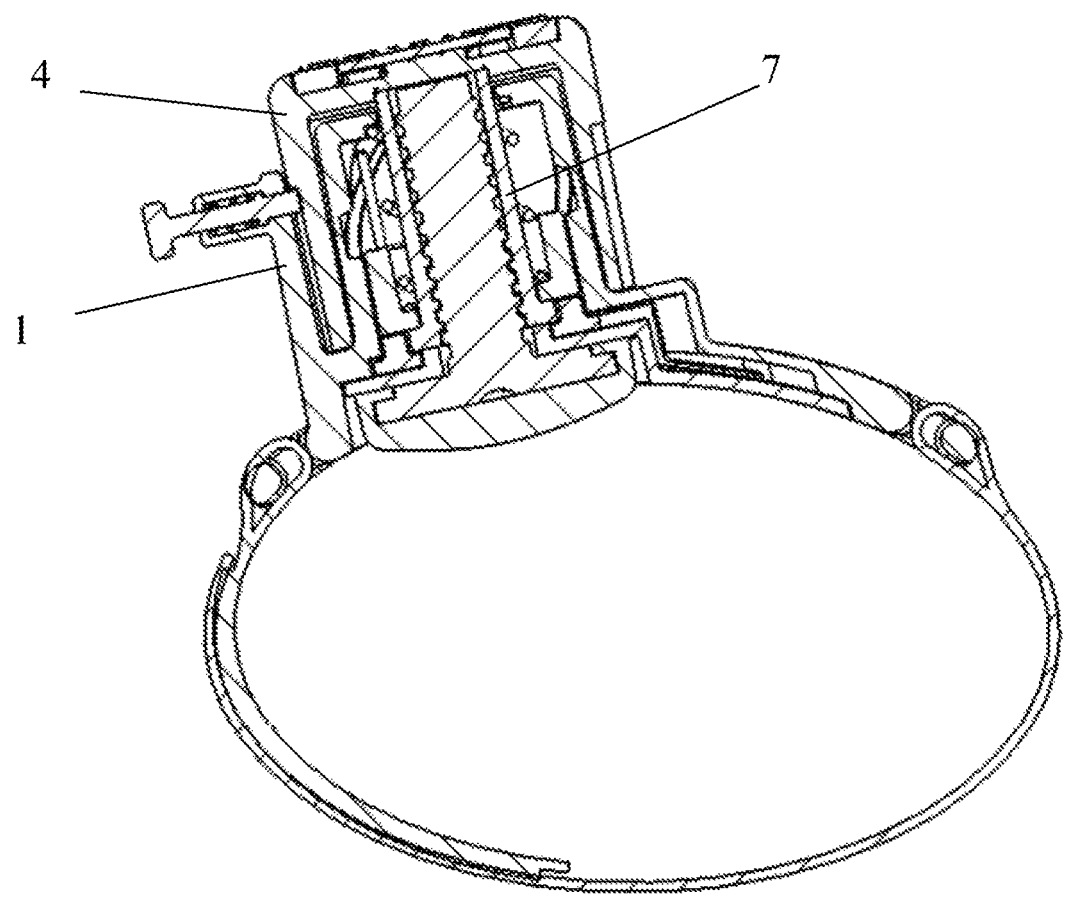
FIG. 24 is a longitudinal cross-sectional view of the tourniquet provided with a rotation locking device in FIG. 22.

The tourniquet of this Example is substantially the same as that of Example 3. The difference is that the floating nut of the tourniquet of this Example is integrated or integrally formed, as shown in FIGS. 22-24. The tourniquet in this Example includes a rotation locking device. The rotation locking device includes a ring of V-shaped groove 24 arranged on the outer periphery of the knob 4, and a spring-mounted wedge pin 23 fixed on one side of the belt plate 1. Wherein, the acute angle formed by the first side of the V-shaped groove 24 and the tangent to the apex of the V-shaped groove 24 is in the range of 5-45 degrees; preferably, 10-30 degrees; more preferably, 15-25 degrees; the acute angle formed by the second side of the V-shaped groove 24 and the tangent to the apex of the V-shaped groove 24 is in the range of 45-90 degrees; preferably, 50-80 degrees; more preferably, 60-70 degrees. As shown in FIG. 23, one end of the spring-mounted wedge pin 23 in contact with the V-shaped groove 24 is formed into a shape complementary to the V-shaped groove 24. The wedge pin 23 is supported by a wedge pin holder 25, which is fixed on the belt plate 1.

When the knob 4 rotates in the first direction (clockwise in FIG. 23), the wedge pin 23 automatically rebounds along the slope of the first side of the V-shaped groove 24, leaving the V-shaped groove 24 on the knob 4, then the knob 4 rotates freely. When the knob 4 rotates in the second direction (counterclockwise in FIG. 23), the wedge pin 23 is engaged with the V-shaped groove 24, and the knob 4 cannot be rotated. Only when the wedge pin 23 is pulled to draw it away from the V-shaped groove 24, the knob 4 can be rotated in the second direction.

By adjusting the angle formed by the first side and the second side of the V-shaped groove 24 with respect to the tangent to the apex of the V-shaped groove 24, similarly, the knob 4 can also be rotated freely in the counterclockwise direction, and engaged when rotated clockwise. Only when the wedge pin 23 is pulled to draw it away from the V-shaped groove 24, the knob 4 can be rotated in the clockwise direction.

In another preferred embodiment, the acute angle formed by the first side of the V-shaped groove 24 and the tangent to the apex of the V-shaped groove 24 and the acute angle formed by the second side of the V-shaped groove 24 and the tangent to the apex of the V-shaped groove 24 are both in the range of 45-90 degrees; preferably, 50-80 degrees; more preferably, 60-70 degrees. This design makes the wedge pin 23 engage with the V-shaped groove 24 and the knob 4 cannot rotate, regardless of whether the knob 4 rotates in the first direction or the second direction. Only when the wedge pin 23 is pulled to draw it away from the V-shaped groove 24, the knob 4 can rotate in the first direction or the second direction.

Example 6

The tourniquet of this Example is substantially the same as that of Example 3. The difference is that the time device of the tourniquet of this Example is an electronic clock. Under the condition that the tourniquet is tied to the patient and starts to stop bleeding, the electronic clock starts timing, and when the tourniquet is removed from the patient and hemostasis is stopped, the electronic clock stops timing, thus the electronic clock displays the duration of hemostasis.

In one embodiment, the electronic clock is started and stopped by the on-off key: when the on-off key is pressed, the timing starts, and then the on-off key is pressed again, the timing stops.

In another embodiment, the electronic clock is automatically timed according to the sensor's sensing: when the sensor detects a human body, the sensor controls the electronic clock to start timing, and when the sensor cannot detect the human body, the sensor controls the electronic clock to stop timing.

Example 7

Figure 25:
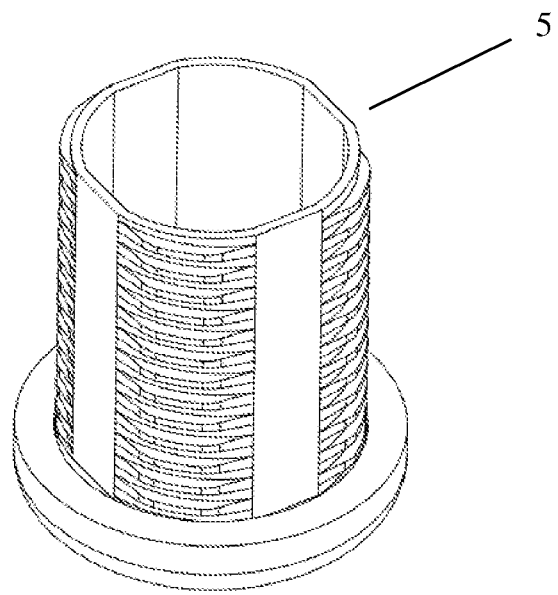
FIG. 25 is a perspective view of a pressure stud in an example of the present invention.

The tourniquet of this Example is substantially the same as that of Example 3. The difference is that the pressure stud 5 of the tourniquet of this Example is a hollow structure, as shown in FIG. 25. Compared with the pressure stud 5 of Example 3, the diameter of the pressure stud 5 of this Example is larger. The diameter of the hollow cavity of the pressure stud 5 in this embodiment is 5-30 mm, preferably 20 mm. Through the hollow design, a visual channel is formed, so that the medical staff can observe the bleeding at the puncture point more clearly through the pressure stud 5 and the hemostatic pad 6, wherein the bottom surface of the pressure stud 5 and the hemostatic pad 6 are transparent.

Figure 26:
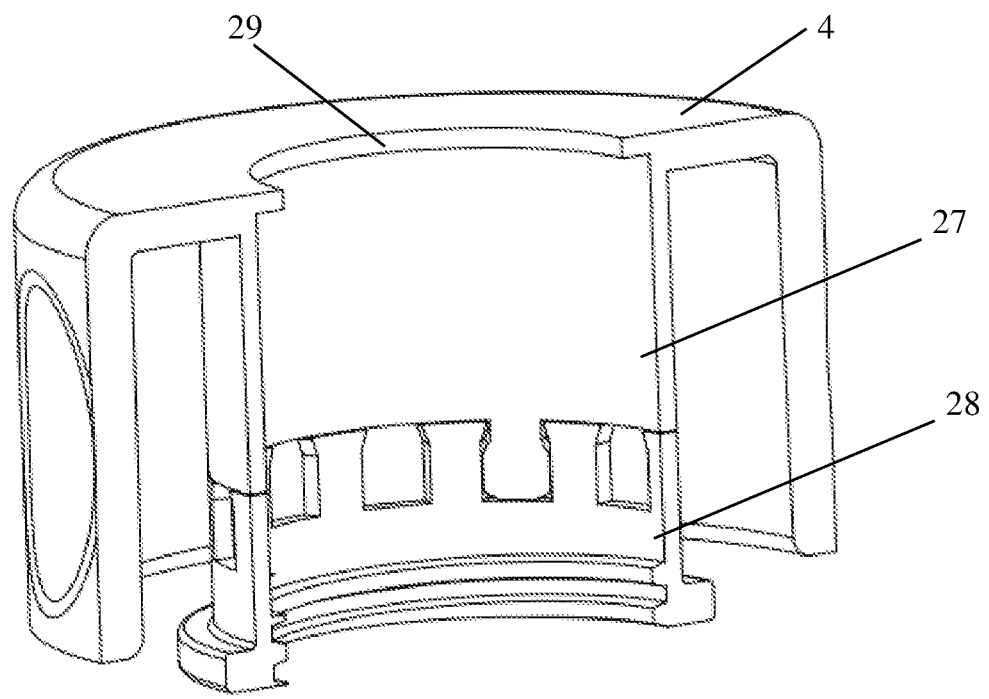
FIG. 26 is a perspective view of a knob provided with a central through hole in an example of the present invention.

At the same time, correspondingly, the part of the top cover of the knob 4 corresponding to the hollow cavity of the pressure stud 5 is provided with a central through hole 29, as shown in FIG. 26, which serves as a part of the visual channel for the operator to observe conveniently.

Figure 27:
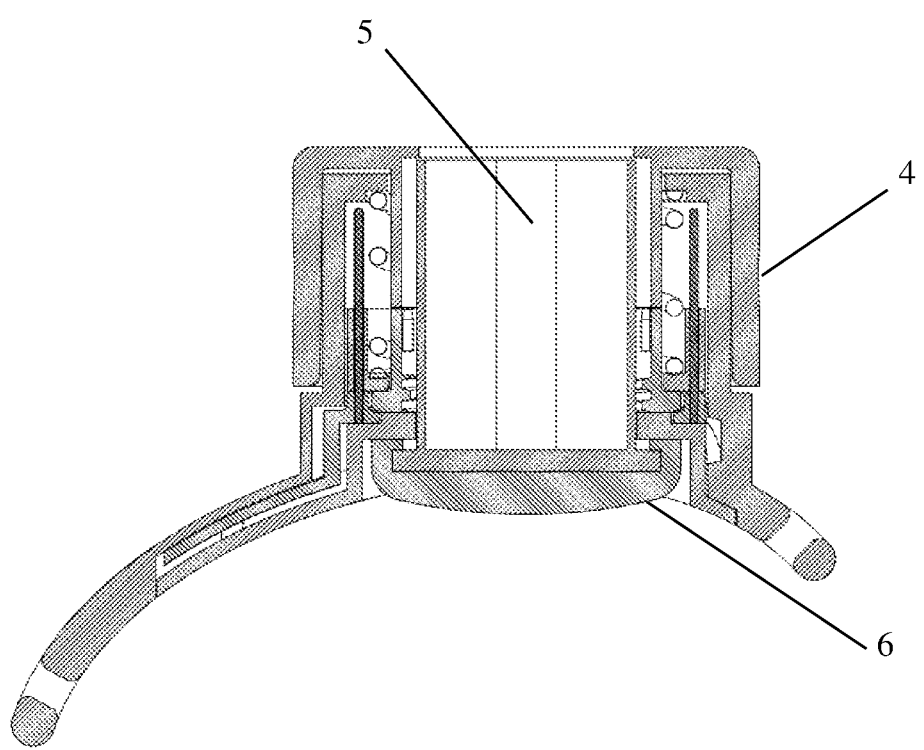
FIG. 27 is a partial cross-sectional view of a tourniquet in an example of the present invention.
Figure 28:
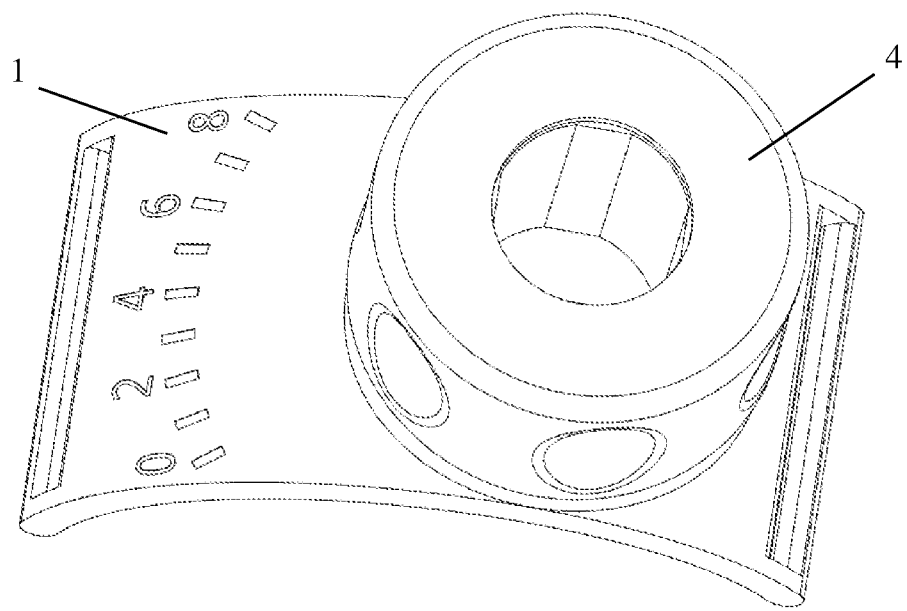
FIG. 28 is a partial perspective view of a tourniquet in an example of the present invention.

FIG. 28 shows a perspective view of the pressure stud 5 in FIG. 25 assembled with the knob 4 in FIG. 26 and other parts of the tourniquet in Example 3, and FIG. 27 shows a cross-sectional view of FIG. 28.

Although the time device is not shown in FIGS. 26-28, it should be understood that the time device (for example, the ring-shaped time dial 26) may be disposed on the ring-shaped area outside the central through hole 29 of the top cover of the knob 4.

In another preferred embodiment, the pressure stud 5 can be made opaque, and one or more through holes are opened on the bottom surface of the pressure stud 5, and the bleeding at the puncture point can be observed through the through hole(s).

All documents mentioned in the present invention are cited as references in this application, as if each document was individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A tourniquet, which comprises
a fixed module including a belt plate and a connecting belt;
wherein the belt plate comprises a through hole, and a protrusion formed by extending upward from a circumferential side of the through hole and retracting inward at a top end to form an annular opening, and both ends of the belt plate are respectively connected to both ends of the connecting belt which has an adjustable length;
a hemostatic module including a knob, a pressure stud and a hemostatic pad;
wherein the knob is wrapped around the protrusion and is rotatable relative to the protrusion;
the pressure stud penetrates the knob and the protrusion, and the upper part of the pressure stud is threadedly connected with the knob, and the lower end of the pressure stud is fixedly connected with the hemostatic pad, and the pressure stud threadedly matched with the knob moves downward by rotating the knob to drive the hemostatic pad to press down; and
an indicating module including a floating nut, a spinning press block, a spring, a connecting piece, a pointer and a dial;
wherein the floating nut is arranged around the pressure stud, with the upper end of the floating nut being fixedly connected to the knob, and the lower end of the floating nut being provided with a support part;
the spinning press block is arranged around the floating nut, with an inner side of the spinning press block abutting against the floating nut, an outer side of the spinning press block being in thread-fit connection with an inner side of the protrusion, and the lower end of the spinning press block being supported by the support part; and the spinning press block is provided with a holding hole penetrating through from top to bottom;
the spring is sheathed outside the floating nut, with the upper end of the spring abutting against a top inner surface of the protrusion, and the lower end thereof abutting against the upper end of the spinning press block;
the connecting piece is disposed in the holding hole, the connecting piece does not rise along with the spinning press block, but rotates along with the spinning press block, and the lower end of the connecting piece is fixedly connected to the pointer;
the pointer is arranged horizontally, and one end of the pointer is fixedly connected to the connecting piece and rotates with the connecting piece, and the other end of the pointer points to different pressure values on the dial.

2. A tourniquet which comprises
a fixed module including a belt plate and a connecting belt;
wherein the belt plate comprises a through hole, and a protrusion formed by extending upward from a circumferential side of the through hole and retracting inward at a top end to form an annular opening, wherein both ends of the belt plate are respectively connected to both ends of the connecting belt which has an adjustable length;
a hemostatic module including a knob, a pressure stud and a hemostatic pad;
wherein the knob is wrapped around the protrusion and rotatable relative to the protrusion, and the knob is provided with a time device for recording the duration of hemostasis; the pressure stud is provided with an external thread, and the lower end of the pressure stud is fixedly connected with the hemostatic pad;
wherein the pressure stud moves downward by rotating the knob to drive the hemostatic pad to press down; and
an indicating module including a floating nut, a spinning press block, a spring, a connecting piece, a pointer and a dial;
wherein the upper end of the floating nut is fixedly connected with the top cover of the knob, and the floating nut is provided with internal threads, wherein the floating nut penetrates the protrusion and penetrates into an inner cavity of the protrusion, and the lower end of the floating nut is provided with a supporting part; wherein the pressure stud is arranged in the inner cavity of the floating nut, and is threadedly connected with the internal thread of the floating nut, wherein rotation of the knob drives the floating nut to rotate, so that the pressure stud threadedly connected with the floating nut moves downward;
the spinning press block is arranged around the floating nut, with an inner side of the spinning press block abutting against the floating nut, an outer side of the spinning press block being in thread-fit connection with an inner side of the protrusion, and the lower end of the spinning press block being supported by the support part; the spinning press block is provided with a holding hole penetrating through from top to bottom;
the spring is sheathed outside the floating nut, with the upper end of the spring abutting against a top inner surface of the protrusion, and the lower end thereof abutting against the upper end of the spinning press block;
the connecting piece is disposed in the holding hole, the connecting piece does not rise along with the spinning press block, but rotates along with the spinning press block, and the lower end of the connecting piece is fixedly connected to the pointer;
the pointer is arranged horizontally, and one end of the pointer is fixedly connected to the connecting piece and rotates with the connecting piece, and the other end of the pointer points to different pressure values on the dial.

3. The tourniquet according to claim 2, wherein the time device is an electronic clock, and under the condition that the tourniquet is tied to a patient and starts to stop bleeding, the electronic clock starts timing, while under the condition that the tourniquet is removed from the patient and hemostasis is stopped, the electronic clock stops timing, and the electronic clock displays the duration of hemostasis.

4. The tourniquet according to claim 2, wherein the time device is a clock paddle, which is in the shape of a ring or a disc, and a time scale is marked on the clock paddle, and the clock paddle is fitted in a groove of the knob and is rotatable relative to the groove, and an indicator mark is further provided on the knob.

5. The tourniquet according to claim 2, wherein the floating nut is integrated or integrally formed.

6. The tourniquet according to claim 5, wherein the tourniquet includes a rotation locking device, which includes a ring of V-shaped grooves arranged on outer periphery of the knob, and a wedge pin loaded with a spring and fixed on one side of the belt plate.

7. The tourniquet according to claim 2, wherein the floating nut includes an upper part and a lower part, wherein the upper part and the lower part are detachably fixedly connected, and the upper part is not provided with threads, while the lower part is provided with internal threads that match external threads of the pressure stud.

8. The tourniquet according to claim 7, wherein the upper part and the lower part are snap-connected, wherein the lower end of the upper part is provided with lower teeth and/or lower grooves, and the upper end of the lower part is provided with upper grooves and/or the upper teeth, and the upper part and the lower part insert the teeth into the grooves to be engaged and fixed by axial pressure, or separate the teeth from the grooves by axial tension.

9. The tourniquet according to claim 2, wherein both sides of the belt plate are curved, so that an inner surface of the belt plate fits an outer surface of a hand for hemostasis.

10. The tourniquet according to claim 2, wherein the pressure stud is a hollow structure which forms a visible channel, so that an operator can clearly observe a bleeding at a puncture point through the visible channel.

11. The tourniquet according to claim 10, wherein a portion of a top cover of the knob corresponding to a hollow cavity of the pressure stud is provided with a central through hole, which is a part of the visible channel.

12. The tourniquet according to claim 11, wherein a bottom surface of the pressure stud and the hemostatic pad are transparent; or
the pressure stud is opaque, and one or more through holes are opened on the bottom surface of the pressure stud, and the bleeding at the puncture point can be observed through the through holes.

13. The tourniquet according to claim 2, wherein the dial has a scale stroke in a range of 5-50 N.

14. The tourniquet according to claim 2, wherein the spring has a wire diameter of 0.5-1.5 mm, a height of 5-30 mm, and a screw pitch of 1-10 mm.

15. The tourniquet according to claim 2, wherein the tourniquet includes a fixed pad, which is used to assist in supporting the tourniquet.

16. The tourniquet according to claim 2, wherein the tourniquet includes a baffle plate, which is fixed to the bottom of the belt plate, the baffle plate and the belt plate enclose a pointer compartment, and the pointer can rotate in the pointer compartment, and the baffle plate is also used for supporting the floating nut.

17. The tourniquet according to claim 2, wherein the pointer is a bidirectional pointer, which includes a rotating ring, a first pointer and a second pointer, wherein a top surface of the rotating ring is fixedly connected to the connecting member, the first pointer extends outward from the rotating ring in a radial direction of the rotating ring, and the second pointer extends from the rotating ring in a direction opposite to the first pointer.

18. The tourniquet according to claim 2, wherein a nominal diameter of the holding hole is larger than a nominal diameter of the connecting piece.

19. The tourniquet according to claim 2, wherein the screw threads for matching the protrusion with the spinning press block have a screw pitch of 20 mm-80 mm.

* * * * *